(12) United States Patent
Williamson, IV et al.

(10) Patent No.: US 7,722,642 B2
(45) Date of Patent: *May 25, 2010

(54) EXTREMELY LONG WIRE FASTENERS FOR USE IN MINIMALLY INVASIVE SURGERY AND MEANS AND METHODS FOR HANDLING THOSE FASTENERS

(75) Inventors: Warren P. Williamson, IV, Loveland, OH (US); Paul A. Spence, Louisville, KY (US); George A. Keller, Grandview Heights, OH (US); Cecil R. Robinson, Hilliard, OH (US); Thomas J. Ward, Columbus, OH (US)

(73) Assignee: Medtronic, Inc., Minneapolis, MN (US)

( * ) Notice: Subject to any disclaimer, the term of this patent is extended or adjusted under 35 U.S.C. 154(b) by 1142 days.

This patent is subject to a terminal disclaimer.

(21) Appl. No.: 10/786,657

(22) Filed: Feb. 25, 2004

(65) Prior Publication Data
US 2004/0167573 A1    Aug. 26, 2004

Related U.S. Application Data

(63) Continuation of application No. 10/052,129, filed on Jan. 17, 2002, now abandoned, which is a continuation of application No. PCT/US99/21459, filed on Oct. 14, 1999, now abandoned, application No. 10/786,657, filed on Feb. 25, 2004, which is a continuation-in-part of application No. 08/802,948, filed on Feb. 21, 1997, now Pat. No. 6,042,607, which is a continuation-in-part of application No. 08/606,343, filed on Feb. 23, 1996, now Pat. No. 5,716,370.

(51) Int. Cl.
*A61B 17/08* (2006.01)
*A61B 17/10* (2006.01)

(52) U.S. Cl. ........................ 606/219; 606/142

(58) Field of Classification Search ................. 606/219, 606/220, 75, 232, 151, 222, 228, 142; 411/457, 411/458, 470, 471
See application file for complete search history.

(56) References Cited

U.S. PATENT DOCUMENTS 2,199,025 A * 4/1940 Conn ...................... 606/232

(Continued)

*Primary Examiner*—Julian W Woo
(74) *Attorney, Agent, or Firm*—Michael Jare; Jeffrey J. Hohenshell

(57) ABSTRACT

Wire fasteners having legs with lengths that can be one hundred times the width of the fastener are used to secure items, such as prosthesis valves to a patient during minimally invasive surgery. The fasteners are manipulated into position and then are immobilized by means of the legs thereof for tensioning, cutting and forming in situ. The fasteners are manipulated, tensioned and formed from the leg end of the fasteners. Tools for initially placing the fasteners and for immobilizing, tensioning, cutting and bending the fastener legs are disclosed. Once the fasteners are initially placed, the prosthesis is placed on the long legs of the placed fasteners and is guided into position on the legs. Once the prosthesis is in position, the legs of the fasteners are immobilized, tensioned, cut and bent into staple-like shapes to secure the prosthesis to the patient. A method for carrying out the procedure using the long fastener is also disclosed. Using the teaching of the present disclosure, a surgeon can customize a fastener to the particular surgery or even to the particular portion of surgery being performed during the surgery.

21 Claims, 28 Drawing Sheets

U.S. PATENT DOCUMENTS

| | | | | |
|---|---|---|---|---|
| 4,203,218 A | * | 5/1980 | Dal Pont | 433/176 |
| 4,453,661 A | * | 6/1984 | Genyk et al. | 227/19 |
| 4,549,545 A | * | 10/1985 | Levy | 606/228 |
| 4,637,194 A | * | 1/1987 | Knowles | 411/471 |
| 5,002,563 A | * | 3/1991 | Pyka et al. | 606/222 |
| 5,219,359 A | * | 6/1993 | McQuilkin et al. | 606/232 |
| 5,366,480 A | * | 11/1994 | Corriveau et al. | 606/232 |
| 5,397,324 A | * | 3/1995 | Carroll et al. | 606/151 |
| 5,972,004 A | * | 10/1999 | Williamson et al. | 606/142 |
| 6,162,233 A | * | 12/2000 | Williamson et al. | 606/142 |

* cited by examiner

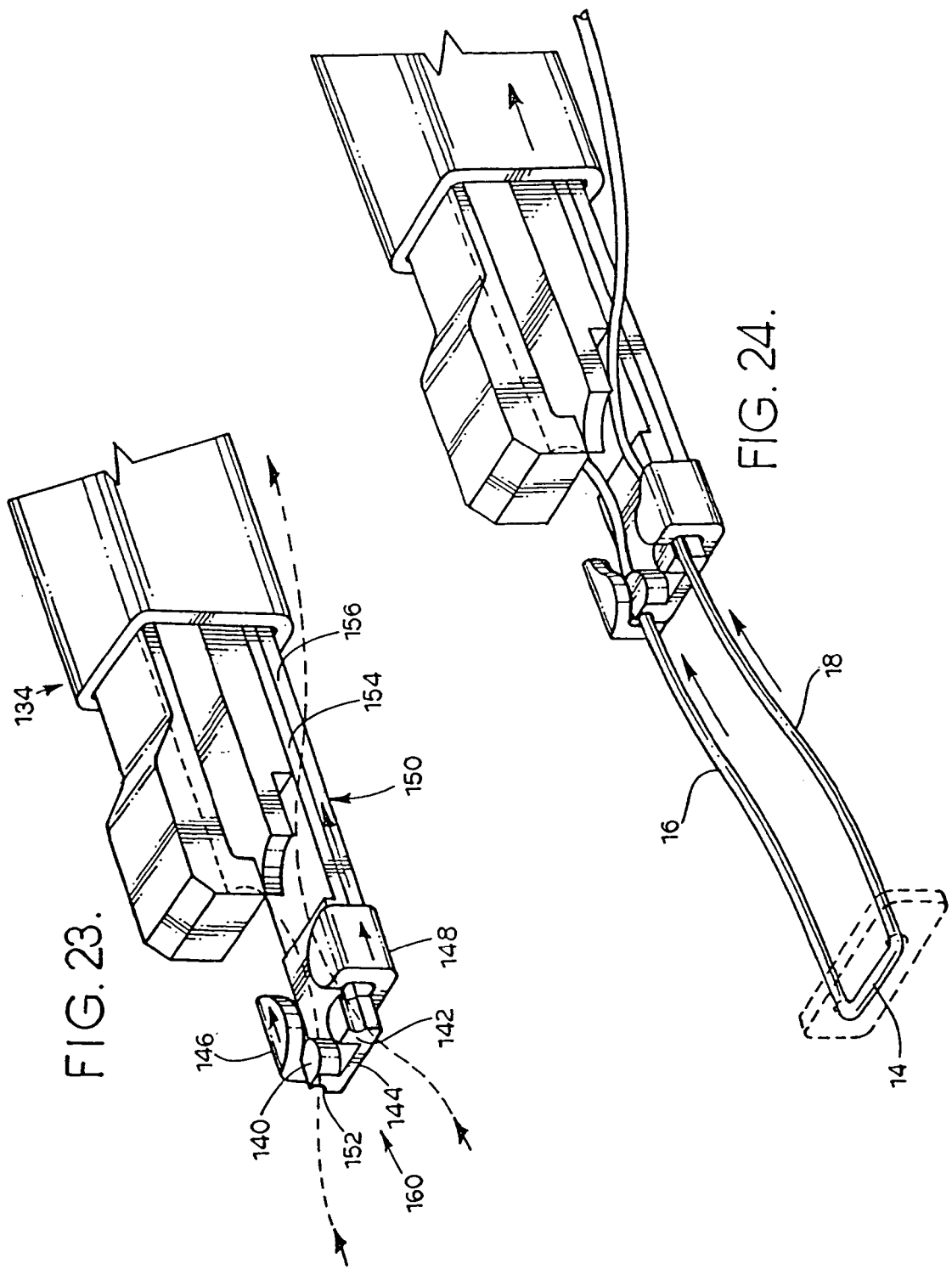

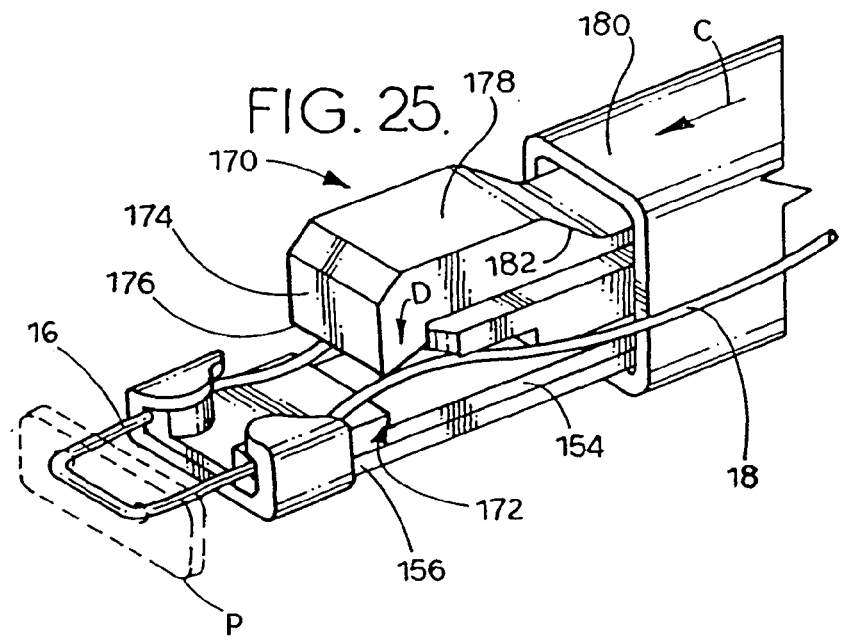
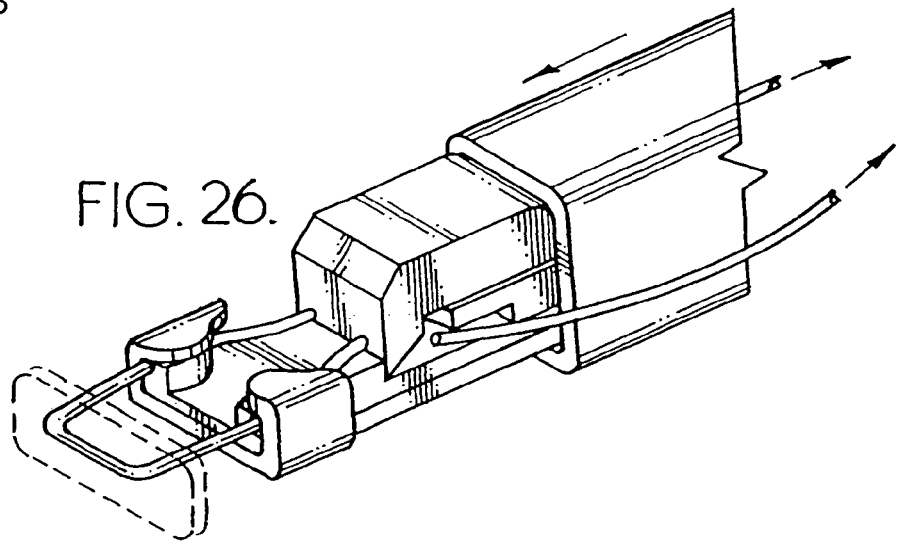

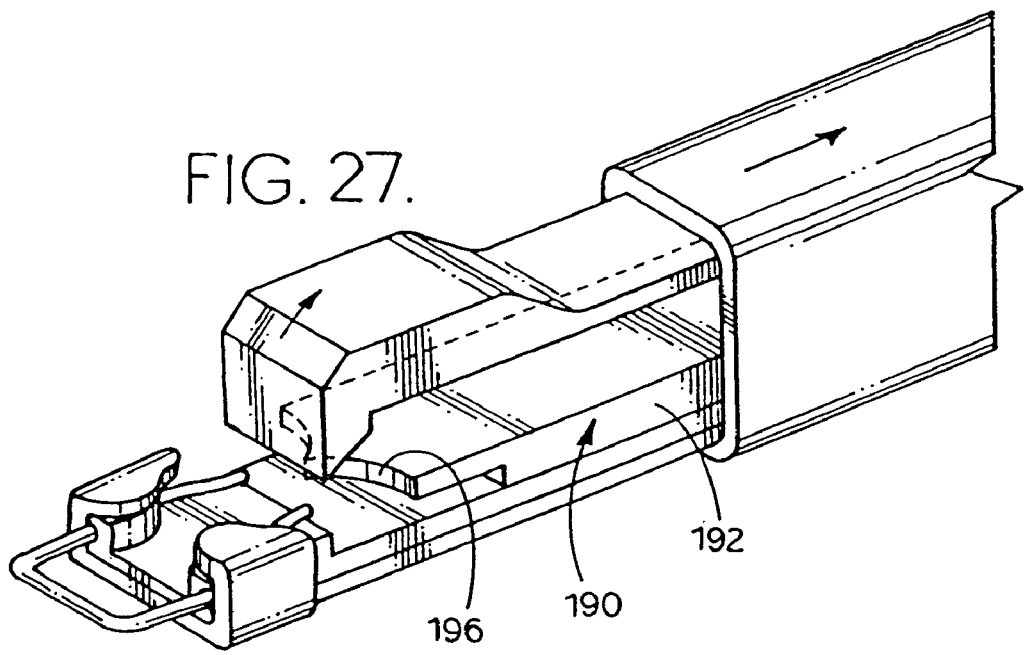
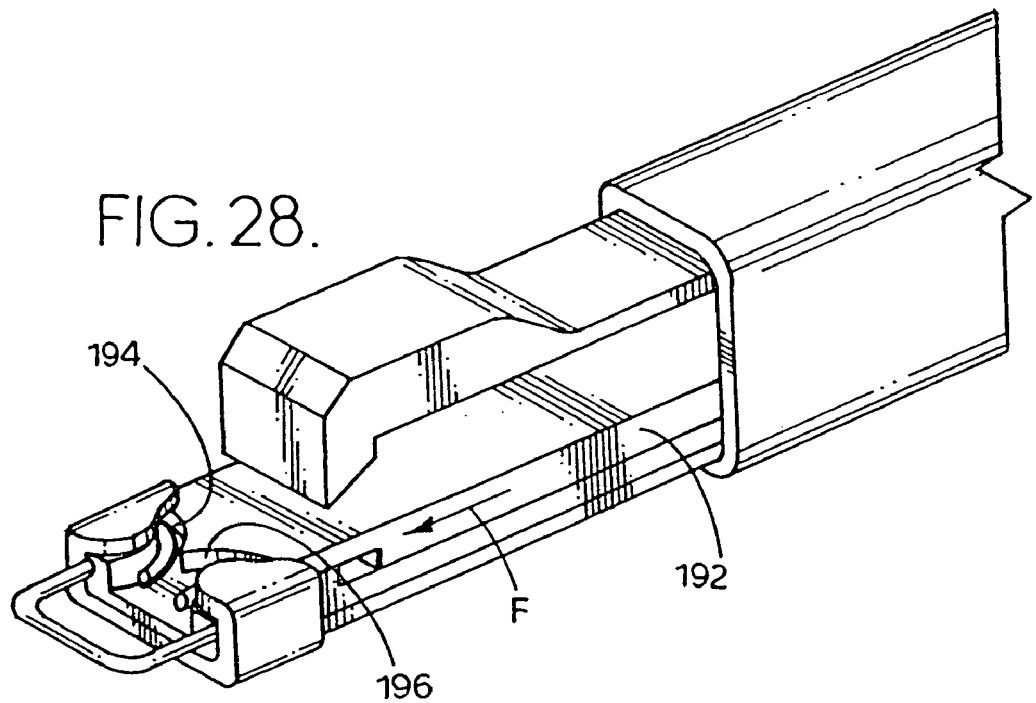

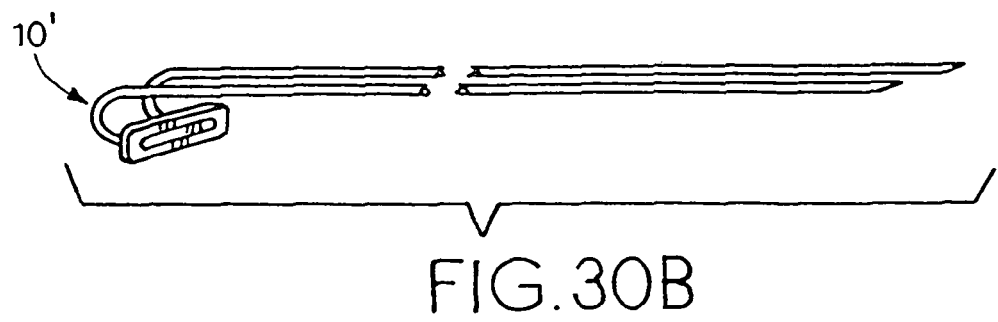
FIG. 30B
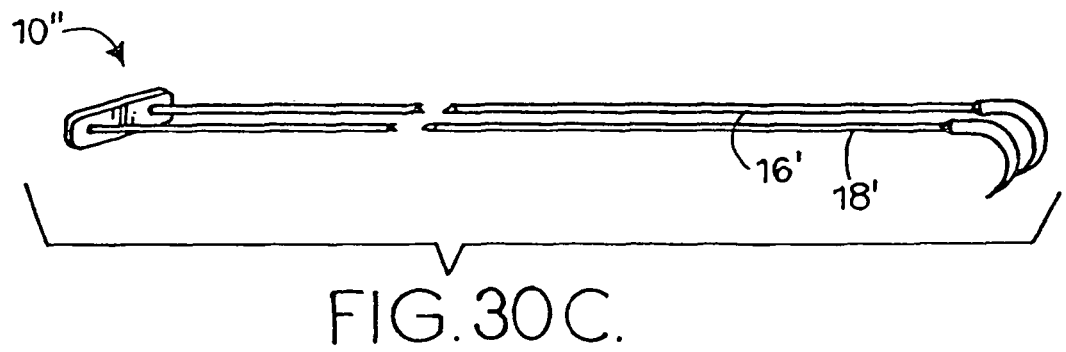
FIG. 30C.
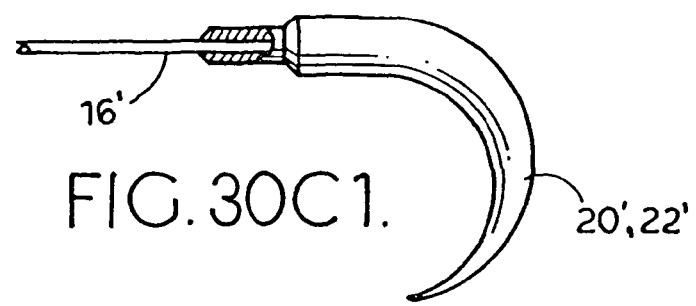
FIG. 30C1.

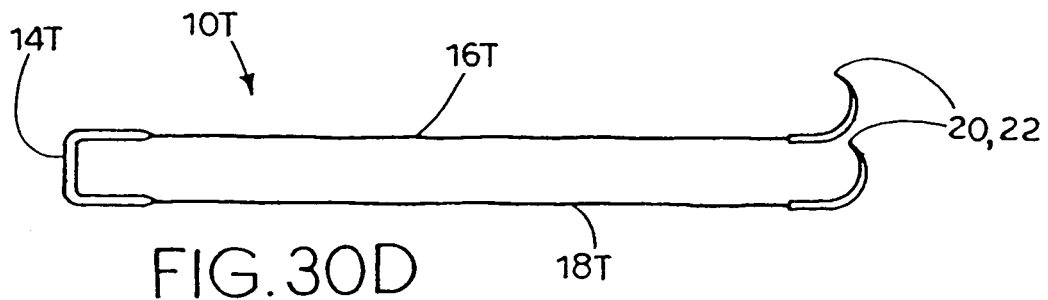
FIG. 30D
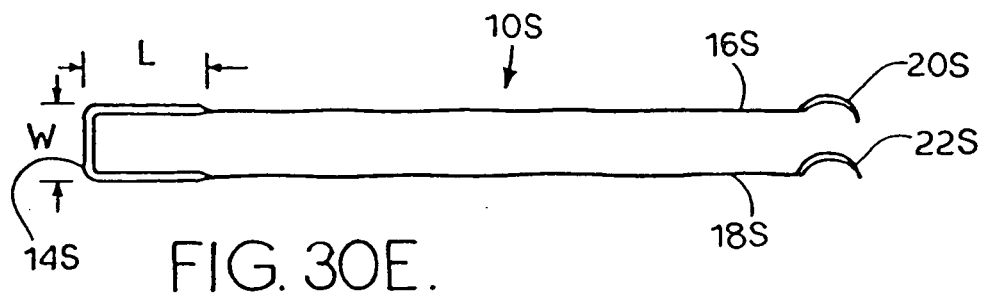
FIG. 30E.
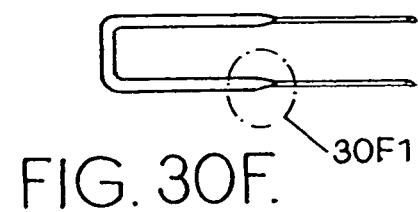
FIG. 30F.
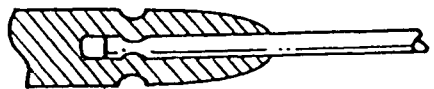
FIG. 30F1.

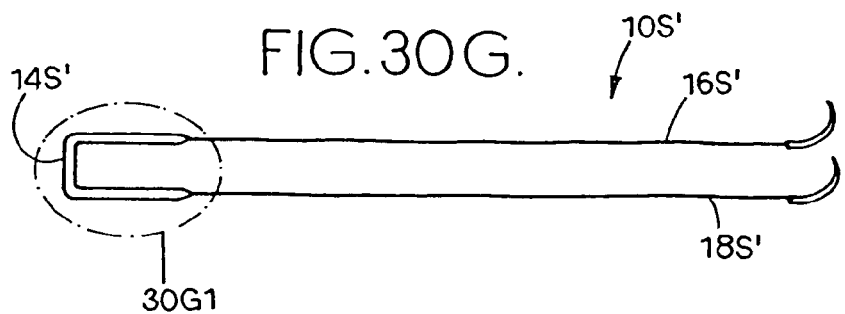
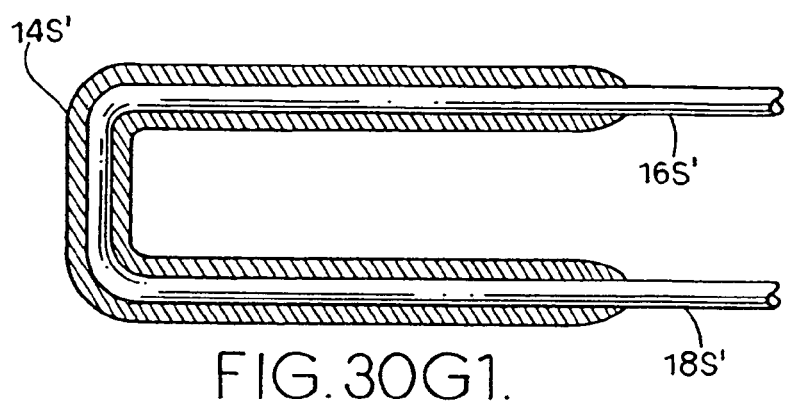
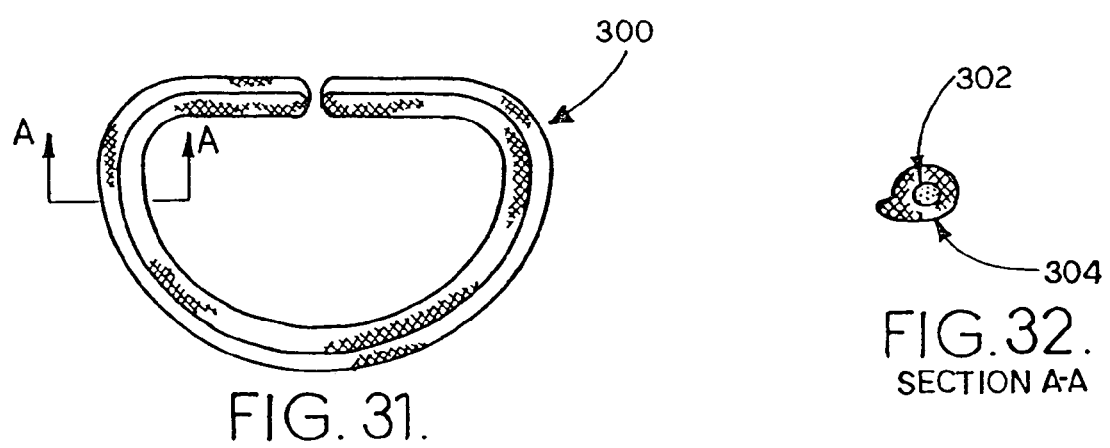

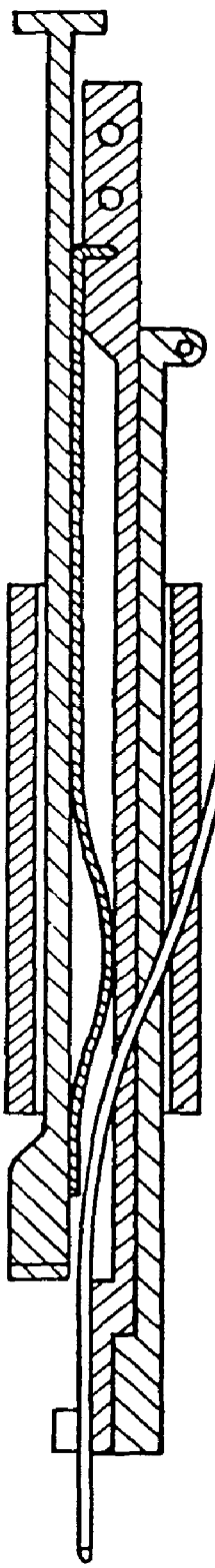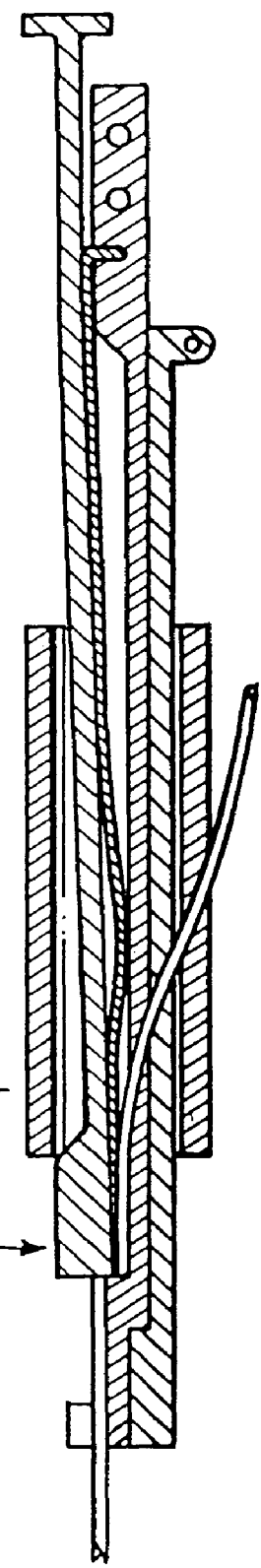

EXTREMELY LONG WIRE FASTENERS FOR USE IN MINIMALLY INVASIVE SURGERY AND MEANS AND METHODS FOR HANDLING THOSE FASTENERS

This application is a continuation of U.S. Ser. No. 10/052,129, filed on Jan. 17, 2002 now abandoned which is a continuation of International Application Serial No. PCT/US99/21459, filed on Oct. 14, 1999 (expired) which claims the priority of application Ser. No. 09/369,196 filed Aug. 6, 1999 (now U.S. Pat. No. 6,162,233). The disclosures of these applications are incorporated herein by reference.

CROSS REFERENCE TO RELATED APPLICATIONS

The present application is a continuation-in-part of Ser. No. 08/802,948 filed on Feb. 21, 1997 now U.S. Pat. No. 6,042,607 which is a continuation-in-part of Ser. No. 08/606,343 filed on Feb. 23, 1996 now U.S. Pat. No. 5,716,370. The disclosures of these applications are incorporated herein by reference.

TECHNICAL FIELD OF THE INVENTION

The present invention relates to the general art of minimally invasive surgery, and to the particular field of fasteners, tools and methods associated with minimally invasive surgery.

BACKGROUND OF THE INVENTION

In recent years, there has been a growing trend toward using minimally invasive surgical techniques to perform heretofore complicated and complex operations. Minimally invasive techniques have therefore been applied to many procedures such as gall bladder removal, operation on the reproductive organs, urological operations, and, more recently, heart valve repair and replacement as well as by-pass operations. Minimally invasive surgery uses only a small incision through which tools are inserted into the patient, with the tool being manipulated from outside the patient. Video is often used so the surgeon can view the surgical site. Minimally invasive surgery has several advantages over other techniques including, inter alia, less trauma to the patient, smaller incisions, less post-operative pain, quicker recovery time (especially in the case of heart surgery since no ribs need to be broken for minimally invasive surgery), shorter time spent in the intensive care unit, as well as other advantages that will occur to those skilled in the art based on the teaching of this disclosure.

The nature of minimally invasive surgery demands several criteria that should be considered for any item used in minimally invasive surgery. This disclosure will focus on fasteners, tools used to place the fasteners, and methods associated with such placement in a minimally invasive surgical procedure. Specifically, this disclosure will focus on fasteners and tools used to place fasteners as well as the techniques for using those tools and fasteners in minimally invasive heart valve replacement surgery. For example, since speed is important for many reasons, the fastener should be capable of expeditious use. However, even though speed is important, the fastener must be capable of reliable and secure placement since a non-secure fastener can have undesirable results, especially if leak-paths could be formed adjacent a non-secure fastener. Still further, any item used for minimally invasive surgery, like any item used for any surgery, should have the confidence of the surgeon. This requires any new item to be useable with techniques and tools that are familiar to the surgeon so he or she need not make large changes in a technique they are already familiar with. It has been observed that surgeons are comfortable in making only incremental changes in technique rather than large scale and sweeping changes in technique. In many minimally invasive procedures, access to the surgical site is of paramount concern. The instrument should be designed to have a minimum bulk and to facilitate action that the surgeon can no longer accomplish with his hands due to restricted access. Since the operation occurs deep inside the patient and the surgeon will have only limited access and visualization of the site, it is important that the tools being used facilitate the procedure as much as possible. In addition, since access is so limited, methods must be effective. There must be a high probability of success in carrying out the techniques for them to be viable and accepted. As mentioned above, heart valve replacement will be used herein as a specific example of a technique that is amenable to minimally invasive techniques. Heart valve replacement using minimally invasive techniques is full discussed in the incorporated applications. While heart valve replacement will be used as the best mode, it is understood that the invention disclosed herein can be used in a myriad of techniques as will occur to those skilled in the art based on the teaching of this disclosure. Accordingly, there is no intention to limit the present disclosure to heart valve replacement only. Still further, the terms "fastener," "anchor" and "staple" as used in this disclosure are intended to be interchangeable. However, those skilled in the art will understand that the term "fastener" can include other elements and a "staple" is a form of fastener. Wire suture is yet another term used to describe the fastener disclosed herein.

As can be understood from the foregoing, there is a need for a means and method for placing fasteners in a minimally invasive surgical procedure that is expeditious but reliable and is small enough to provide a clear sight path and be manipulated by a surgeon in small areas, yet will be secure when placed and will have the confidence of the surgeon.

As disclosed in the incorporated applications, heart valves can be installed with double lead sutures with a pledget and needles on the end of each suture lead. As further discussed in these applications, each suture needle can be independently placed through the annulus of a patient's tissue and the free ends brought up outside the cavity. Pairs of these sutures are placed, according to the teaching of the incorporated material, circumferentially around the annulus where the old valve has been excised. Once all of the sutures are placed, the needles are then passed through the sewing cuff on the prosthetic heart valve. The prosthesis heart valve is then slid down the associated suture into place in the annulus and the knots tied according to the teaching of these disclosures.

In accordance with these disclosures, there is a need for a fastener, tools and methods which can take advantage of the advances disclosed and taught in the incorporated disclosures.

Currently, some companies have been making tools to facilitate suturing of heart valves for minimally invasive procedures. These include modifications of existing needle driver (forceps) technology or devices to hold the sutures in an organizer to help facilitate the procedure. The problem is that a long needle driver needed for the minimally invasive access makes it difficult to manipulate the tools and even more difficult to tie knots at a remote location and there is little time savings realized. Surgeons therefore have had a difficult time replicating their current techniques with subtle improvements to their existing tools when modified for minimally invasive surgery. For instance, when a surgeon places and drives a needle, the path of motion the needle takes through the patient's tissue is on an arc, with the center of the arc determined roughly by the radius of curvature of the needle. In a minimally invasive surgery procedure, one cannot twist the needle driving forceps in the same path as one does when using the "open procedure" instruments. This is due in part to the limited space associated with minimally invasive surgery. Also, this is due to restricted "in-line" viewing which is all one can obtain when viewing down a small and narrow tunnel-like incision used in minimally invasive surgical procedures. In addition, some surgeons may, in some procedures, want control of the number of sutures used and the location of each of those sutures. In other words, the procedure will most likely take longer and require greater surgeon skill than would a standard non-minimally invasive operation. This will hamper the growth of minimally invasive procedures.

Therefore, there is a need for a fastener and tool for placing the fastener that will be readily adopted by surgeons practicing minimally invasive surgery, such as heart valve replacement surgery.

Still further, it is very undesirable for a suture to come out of the tissue or the item being anchored to the tissue. This can be a problem in older patients with brittle or frail tissue. Therefore, the stress (force per unit area) placed on the tissue by any device used to anchor another device to the patient should be as low as possible. This can be achieved by either reducing the amount of force applied to the tissue or by increasing the area of force application. However, this stress reduction must not occur at the expense of a secure anchor and a leak-proof joint. In the case of a heart valve replacement, the fluids present will be pressurized blood, which cannot leak, and in the case of an installation of a prosthesis in the gastro-esophageal tract, the fluids may include bile fluid and other digestive tract contents, also which cannot be permitted to leak. Thus, a leak free joint is essential, but cannot be obtained at the expense of tearing the patient's tissue. Thus, the amount of force applied is not easily reduced.

Therefore, there is a need for a fastener that can increase the total area of force application in an anchor situation without unduly sacrificing other advantages such as a good blood seal between the prosthesis and the patient's tissue.

Yet a further problem with some prosthetic heart valves and the prior implanting procedures associated therewith is that there are unwanted projections remaining on the implanted item. These projections are created when sutures currently used in such procedures are knotted on the implanted item. This is especially true for valves that are sutured in place. Blood clots tend to form around foreign objects in the body. The body's natural defenses try to seal off any foreign material and make it non-threatening. However, there is a danger that the formed blood clots may dislodge into the patient's blood stream which may cause a major problem such as stroke.

The sutures used in many existing techniques to sew a cuff in place are knotted and cut off. This leaves raw edges exposed to the patient's blood stream. These raw edges of the cut-off suture and knot provide surfaces for clot formation and since they are flexible and are directly in the high pressure blood flow path, they provide potential for clots to break off into the bloodstream. Loose clots in the bloodstream are dangerous for the patient as they have the potential for producing a stroke. Clots forming on sutures may also extend into the valve and produce malfunctions by trapping the valve open or shut. It is common practice to treat a post-surgical patient with heparin or some other anticoagulant to minimize the production of clots, short term. For longer term anticoagulant thereby, the patient with a mechanical heart valve prosthesis faces a life long requirement of use of a low grade anticoagulant such as Cumenden®.

Still further, the exposed surfaces can become a site for infection. Circulating bacteria may become attached and lead to infection at the implanted device. Such infections are notoriously difficult to treat with antibiotics.

Therefore, there is a need for a means and method for placing an item, such as, for example, a heart valve, in a patient during minimally invasive surgery that minimizes the amount of foreign objects that remain exposed to the patient after the item has been implanted.

As known to those skilled in the art, prior art sutures require knots. In the case of knots, proper tension is extremely important. Most surgeons determine the tension in a suture knot by feeling the knot with their finger. However, in the case of minimally invasive surgery, the surgeon cannot get his or her hand into position to feel the knot and thus ensure proper tension.

Therefore, there is a need for a fastener that can ensure proper tension in minimally invasive surgery without requiring a surgeon to touch the fastener to make this determination.

Still further, installing multiple suture pairs can be time consuming and can be difficult. Anything that can shorten the time of a surgical procedure can be advantageous. Therefore, there is a need for a fastener that can be quickly placed yet will still permit a surgeon to have great control of the suturing process and pattern, especially the placement of multiple suture pairs.

There is data available which indicates that because the suture is manipulated with the surgeon's gloved hand during the knot-tying process required by prior art procedures, it is susceptible to contamination from pin hole leaks in those gloves. A system which minimizes the direct contact between the surgeon's hand and any of the implanted items will reduce the potential of the development of infection due to contamination.

Therefore, there is a need for a fastener and a means for implanting that fastener which can minimize direct contact between a surgeon's hand and the item being implanted or any component of such implanted items.

Still further, since many patients have variations in size and spacing for the tissue to which an item is being anchored, the surgeon may want to customize the attachment, by, for example, adding fasteners to create just the right spacing and pattern to produce a desired seal for the item.

Therefore, there is a need for a means and a method for placing fasteners which will permit a surgeon to customize the anchoring features of the system.

Still further, some patients have tissue that is thicker than other patient's tissue, or is more fragile than other patient's tissue or the like. If the fastener being used to attach a prosthesis to a patient's tissue has legs that have a predetermined length relative to the base or crown of the fastener, that fastener may be suitable for tissue that has one thickness but not for tissue that has a different thickness. The same situation applies to the amount of tension that is to be applied to the tissue by the fastener. That is, one patient's tissue may be able to withstand more stress than another patient's tissue. Thus, a fastener that is suitable for one patient's tissue may not be suitable for another patient's tissue.

However, the prior art fasteners have legs that are of a preset length. Thus, the surgeon must guess or anticipate what fastener he or she will use in a particular operation, or change fasteners during the operation. This is cumbersome and inefficient. A need might even arise in which different fastener leg lengths are needed for the same patient during a single operation.

Therefore, there is a need for a fastener that can be customized for each particular patient, and each particular application, and can be altered as necessary during a single operation.

OBJECTS OF THE INVENTION

It is a main object of the present invention to provide an anchoring and termination system that can be used in minimally invasive surgery.

It is another object of the present invention to provide a fastening system that can be used in any prosthesis operation.

It is another object of the present invention to provide a fastening system that can be customized for a particular patient.

It is another object of the present invention to provide a fastening system that can be customized for a particular patient during an operation.

It is another object of the present invention to provide a prosthesis anchoring system which utilizes a metal fastener whereby the entire crown of the fastener is used as the retaining surface for the fastener while being terminated from the open leg ends.

It is another object of the present invention to provide a wire fastener that can be terminated with access only to the free legs thereof.

It is another object of the present invention to provide a fastener deployment system which can accurately place a fastener in tissue given minimal access size with superior visual access to the fastener placement.

It is another object of the present invention to provide a fastener for attaching a prosthesis to tissue whereby the fastener starts in a very elongated configuration is cut and terminated in a much shorter configuration.

It is another object of the present invention to provide a fastener having very long legs which extend substantially in the proximal dimension to allow continued access to the extended length of the fastener.

It is another object of the present invention to provide a fastener for use in minimally invasive surgery which establishes the proper retention force without requiring tactile contact between the surgeon and the fastener.

It is another object of the present invention to provide a fastening system whereby the pre-placement of an elongated fastener can guide a prosthesis to a seated position.

It is another object of the present invention to provide a an elongated metal fastener which combines tissue penetrating features with tissue retaining features.

It is another object of the present invention to provide a fastener terminating device and method which terminates a fastener by first gripping the fastener legs spaced from the crown of the fastener then cutting the fastener to length and subsequently forming the fastener.

It is another object of the present invention to provide a device which grabs the fastener legs independent of the fastener crown for formation of the fastener legs.

It is another object of the present invention to provide a prosthesis fastening system which minimizes the protruding mass extending beyond the prosthesis whereby the extending portion of the fastener is minimized in the blood flow area.

It is another object of the present invention to provide a fastener termination means which has a sufficient retention force to securely fasten the prosthesis.

It is another object of the present invention to provide a fastener deployment device which first deploys a fastener in the distal direction penetrating tissue and returning the fastener to a proximal position.

It is another object of the present invention to provide a fastener termination system which is faster than knot tying.

It is another object of the present invention to provide a fastener deployment device which houses a cartridge which in turn houses an elongated metal fastener for deployment in tissue.

It is another object of the present invention to provide a fastener termination device which first attaches to the fastener in a very proximal position away from the item being anchored in the patient, which then is approximated to the item for the termination procedure.

It is another object of the present invention to provide a fastener and a means and method of placing that fastener that improves the efficiency of the methods disclosed in the incorporated applications.

SUMMARY OF THE INVENTION

These, and other, objects are achieved by a metal fastener having very long legs that are immobilized, cut and manipulated to form a fastener that anchors a device, such as a prosthesis, into a patient. The fastener is immobilized and manipulated by a tool that grasps the legs at locations that are spaced from the crown of the fastener. The fastener thus formed has no knots or other elements that project into the patient's blood stream in a manner that is likely to cause blood clots.

It is noted that the best mode of the means and method embodying the present invention is in minimally invasive surgery. However, those skilled in the art will be able to apply the teaching of the present invention to applications other than minimally invasive surgery without departing from the scope of the present invention. For example, open surgery can be performed using the means and method of the present invention, and such application is intended to be encompassed by the present invention.

The long metal fasteners of the present invention are in essence a metal fastener which has about the same crown width as a large staple fastener. However, the legs of the fastener of this invention, instead of having a length approximately half the width of the crown, are many times the width of the crown. As used herein, the "width" of the fastener is the distance from one end of the crown to the other or the distance between points on the crown that are spaced the farthest from each other. Thus, in the case of a circular crown, the "width" will be equal to the diameter of the crown, and in the case of an oval crown, the "width" is the distance between ends of a major diameter thereof. As mentioned above, in the case of a linear crown, the "width" is the distance from one end to the other, and if the fastener has two legs, the "width" of the fastener is the distance between the two legs at the crown if the legs are located on the ends of the crown. If the legs are spaced from the ends of the crown, the "width" will exceed the space between the legs. For example, a large staple having two legs, one at each end of the crown, may have a crown width of approximately 0.2 inches so the legs will have a length of approximately 0.1 inches. However, in the present invention, the fastener legs of a two-legged fastener with a linear crown are long enough to extend out of the patient when the crown is in anchoring position. Thus, for example, even if the crown has a width of approximately 0.2 inches, the legs of the fastener of the present invention can be as much as ten to twenty inches long. The end of each leg is sharpened to a point so that they can easily penetrate tissue and/or any prosthesis attachment fabric or the like. Once the fasteners with the long legs are accurately placed, terminating the legs will complete the anchoring procedure. Unless otherwise noted, the best mode contemplated by this disclosure concerns a two-legged fastener with each leg being located on one end of the crown so the width of the fastener is the distance between the legs. However, a fastener having a single leg will also come within the teaching of the present disclosure, and such a one-legged fastener is intended be covered by this disclosure as well.

As used herein, length of the legs will be defined as the distance between the end of the leg and the crown measured along the long axis of the leg. For the sake of convenience, the ratio of the length of the legs to the width of the fastener will be referred to as the L/W ratio. Thus, using the just-mentioned dimensions, the L/W ratio of the fastener of the present invention is between 50 and 100. In fact, this ratio can be several hundred in some circumstances. As also used herein, a fastener which is referred to or described as, a having a long leg will be understood to be a fastener having an L/W ratio of ten or more. Still further, the term "crown" is used herein as the element that abuts the patient's tissue and resists the tension associated with the fastener. In order to encompass all such elements, the term "crown" is not meant to be restrictive and refers to a fastener base which satisfies the tension-resisting function just described. Also, it is noted that the base can have any shape, including linear as well as an arcuate perimeter. As used herein, the term "arcuate" is intended to mean any element having a shape a portion of which is non-linear. In the case of an arcuate perimeter, the width dimension will be the longest dimension, such as a diameter for a circular perimeter or the major dimension for an arcuate, non-circular perimeter. It is also noted that while the fastener described herein will be described as a wire fastener, no limitation to a metal type material is intended, and any stiff material that will satisfy the requirements associated with the functions set forth herein is intended to be included in this description of the fastener as being "wire." Furthermore, the fastener of the present invention need not be formed of a single, monolithic, material. The fastener can be formed of several materials, it can be formed of a composite material or the like without departing from the scope of the present invention as will occur to those skilled in the art based on the teaching of this disclosure, such as the disclosure associated with FIGS. 30C, et seq below. This feature of the fastener will permit the fastener to be customized for a particular surgery, as was discussed above, and will permit a surgeon to customize and modify the fasteners during a particular surgery whereby the most efficient and effective fastener will be placed where it is most efficient and effective. The only requirement of the fastener is that the legs can be manipulated and bent into a formed configuration and, once bent will retain the bent shape. As used herein, the term "no material memory" is intended to mean a material that can be bent and will retain the bent shape. This material will also be described as being formable.

As will be understood from the teaching of the present disclosure, each fastener leg has a pointed end when it is initially placed into the patient and drawn through the patient's tissue, and then has another end after it has been cut. The cut fastener leg is bent into the formed configuration. The L/W ratio of the formed fastener is substantially that of a common staple, with the length of the formed fastener leg being measure between the cut end of the leg and the crown and is measured along the long axis of the leg. That is, the L/W ratio of the formed fastener is between 1 and ½; whereas, the L/W ratio of the uncut and unformed fastener can be as much as 100 or more.

The fastener of the present invention permits the surgeon to take advantage of the teaching of the incorporated applications. The ends of the fasteners are pushed back into the prosthetic cuff and do not protrude above the surface of that prosthesis. The incidence of clot formation as discussed above will be greatly reduced. In addition, no longer is a site readily available for the attachment of bacteria. By completely eliminating the requirement of manual knot-tying by the surgeon, and replacing it with the mechanical manipulation of the fastener with sterile surgical instruments, the risk of infection is reduced.

In essence, the means and method embodying the present invention comprises three main components: the wire fastener used as an implantable anchoring system for items such as prostheses, means to deploy the wire fastener, and means to manipulate, terminate and form the wire. The anchoring of the prosthesis is securely retained in the tissue and the prosthesis is permanently attached to the tissue. Sutures are in essence tension members which are used to compress the patient's tissue against the prosthesis to seal the prosthesis to the patient's tissue. The fastener of the present invention provides the tension that is required to compress the tissue and adequately terminates the tension member and thus holds the prosthesis in place against the tissue.

As discussed in the incorporated material, some of the most difficult problems facing a surgeon in a minimally invasive procedure are those of minimal access and visibility to the surgical site as well as the inability of the surgeon to feel the tissue and manipulations thereof. These challenges include being able to accurately place tools and sutures. The means and method embodying the present invention provide means and method for tensioning an anchoring system without requiring that a knot be tied and is thus advantageous for minimally invasive surgeries.

In a minimally invasive procedure, the restricted ability to visually inspect the attachment site and the reduced ability to get large instruments to the surgical site puts constraints on the types of instruments that can be used for this type of surgery. By being small and narrow, the means of the present invention which deploys the anchoring system will not block the surgeon's view, yet is also very precise in the way it delivers the anchoring device so that the surgeon can accurately place the anchor into the appropriate anatomy.

The method embodying the present invention encompasses two major steps: surgical access and precise fastener placement in the patient's tissue (attaching the prosthesis to the fastener as necessary); and appropriate termination and forming of those fasteners in such a way that permanently attaches the prosthesis.

The incorporated applications have taught means and methods to secure a heart valve prosthesis with various types of fasteners. In these incorporated disclosures, most of the fasteners are delivered and terminated (or formed) all from one side of the prosthesis. Most commonly, the fastener will be driven or placed into the tissue from the proximal side of the prosthesis (from the surgeon's point of view).

Since most surgeons are familiar with placing metal needles through a patient's tissue, it is advantageous to be able to provide an instrument that can deliver a fastening element in much that same manner as a standard needle. The means and method of the present invention achieve this goal.

BRIEF DESCRIPTION OF THE DRAWING FIGURES

FIG. 23 shows the end of the tensioning tool in position to receive the legs of the fastener.

FIG. 24 shows the end of the tensioning tool capturing the legs allowing the tool to slide down the legs without falling off.

FIG. 25 shows the tensioning tool just as it cuts the legs of the fastener.

FIG. 26 shows the tensioning tool just as it cuts the legs of the fastener.

FIG. 27 shows the tensioning tool in position after the legs have been cut and prior to the cut legs being bent over into staple-forming position.

FIG. 28 shows the tensioning tool as the tool bends the cut and immobilized legs over into the formed configuration.

FIG. 30B is another form of the fastener having a J-shaped body adjacent to the crown.

FIG. 30C is another form of the fastener which includes an arcuate pointed end attached to the pointed end of a fastener leg.

FIG. 30D shows an alternative form of fastener with narrowed extended legs.

Figure 1:
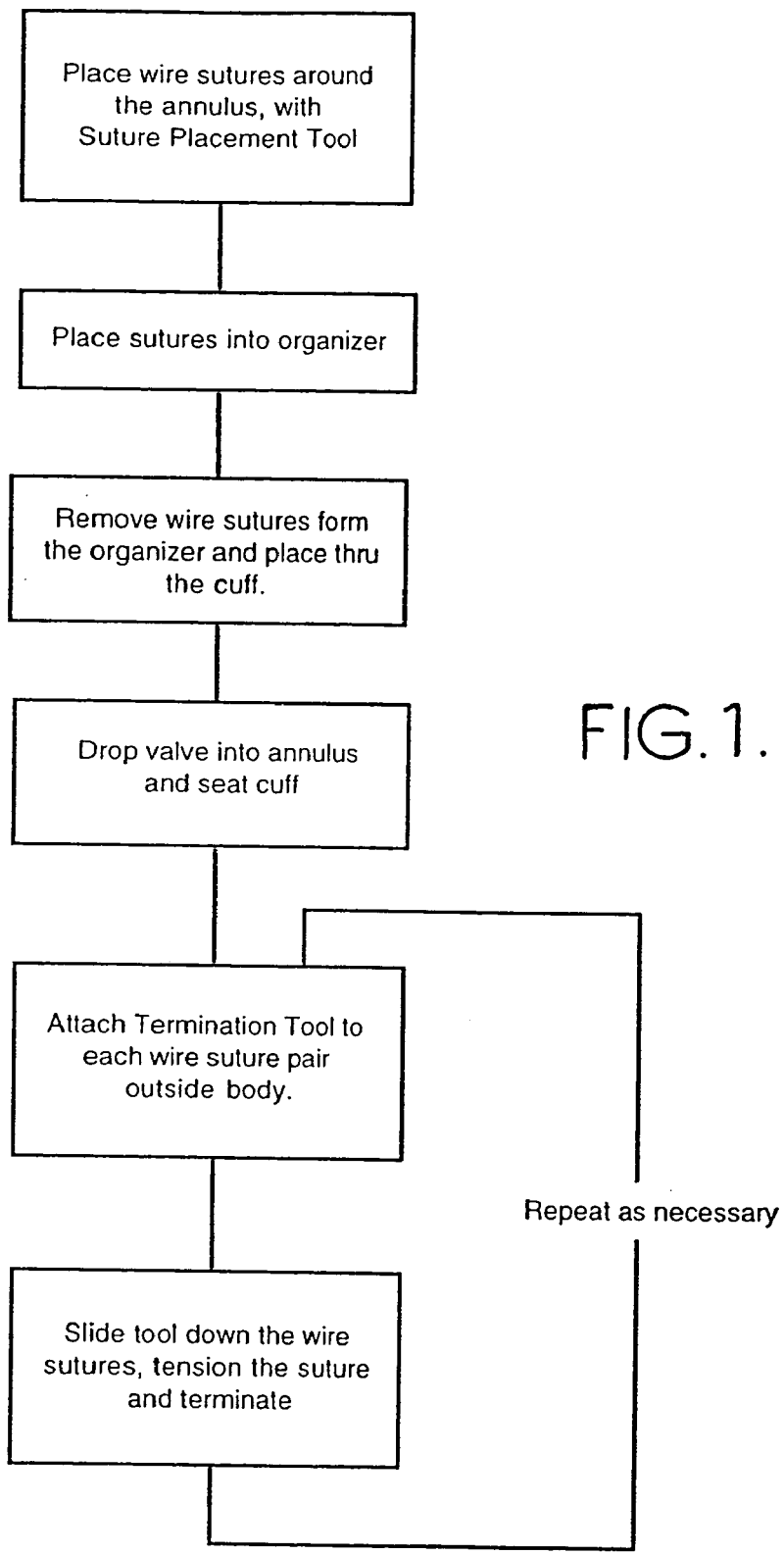
FIG. 1 is a flow chart showing the steps in the method embodying the present invention.

FIG. 30C1 shows the arcuate point of the fastener form shown in FIG. 30C.

FIG. 30E shows a fastener formed of two materials.

FIG. 30F shows a detail of the fastener shown in FIG. 30E.

FIG. 30F1 shows a detail of the fastener shown in FIG. 30F.

FIG. 30G shows another form of fastener formed of two materials.

FIG. 30G1 shows a detail of the fastener shown in FIG. 30G.

FIG. 31 is a top view of a mitral valve anuloplasty ring that can be installed using the means and methods of the present invention.

FIG. 32 is a view taken along line A-A of FIG. 31.

Figure 33:
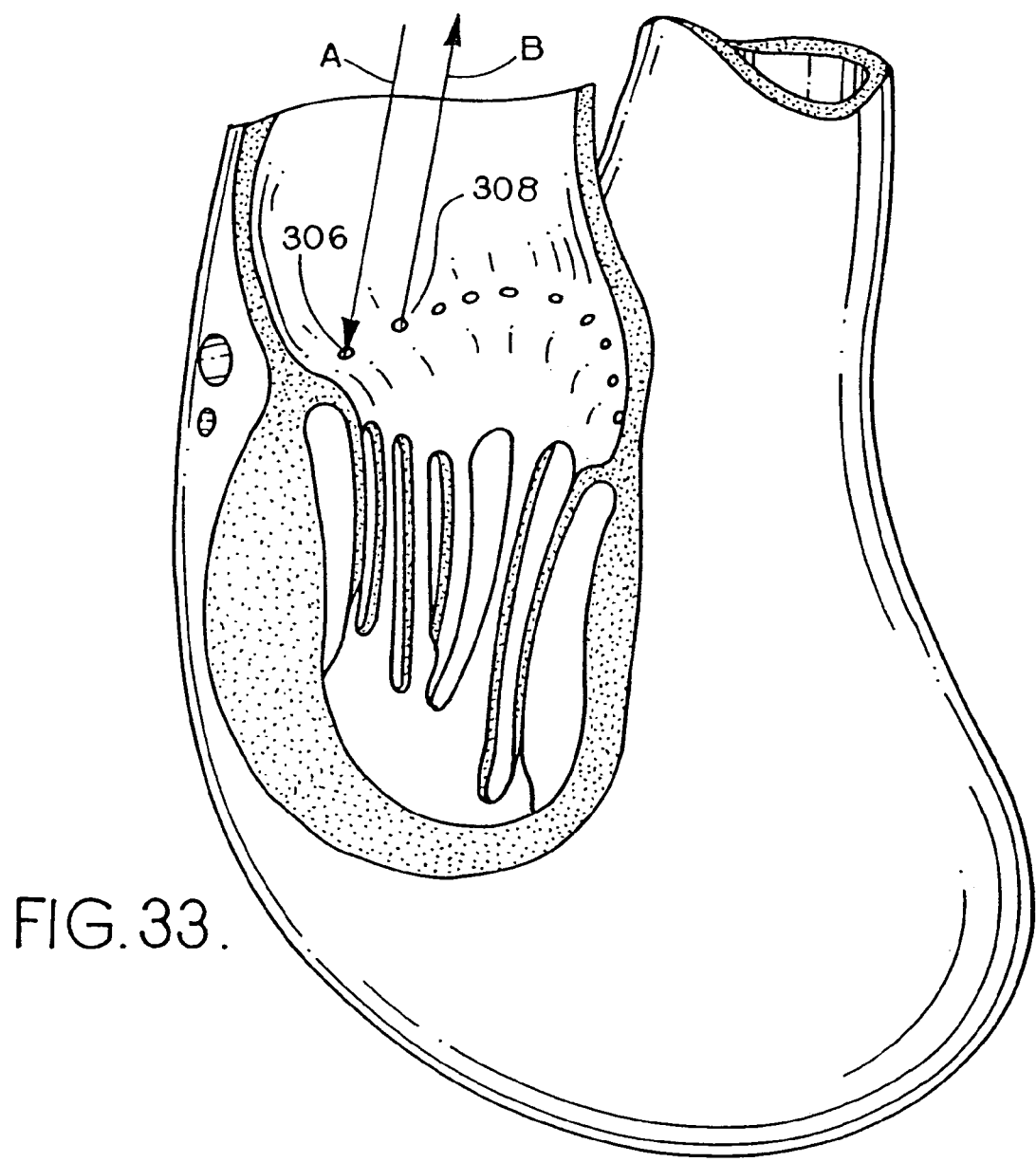

FIG. 33 shows a cut-away view of a mitral valve.

Figure 34:
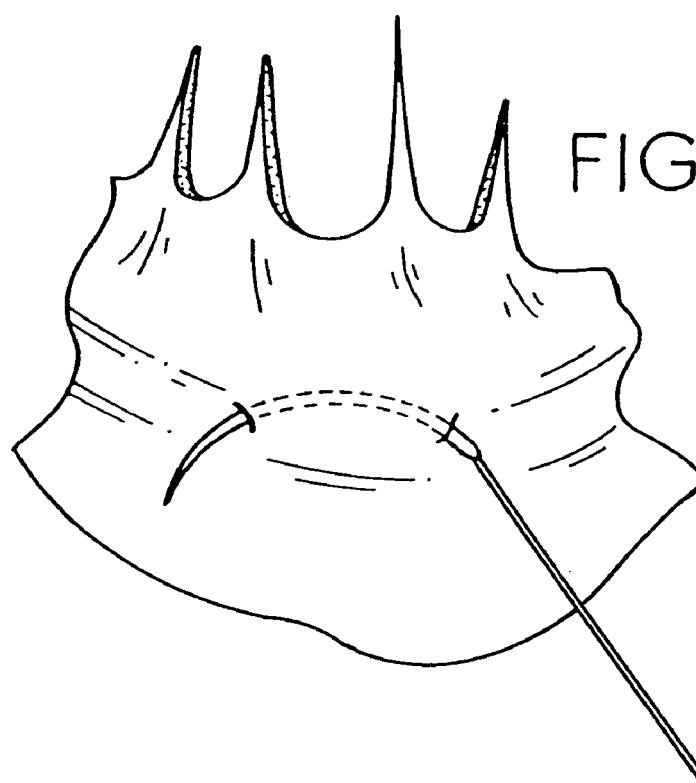

FIG. 34 shows a wire fastener of the present invention with the curved pointed end penetrating the mitral valve annulus during installation according to the method of the present invention.

Figure 35:
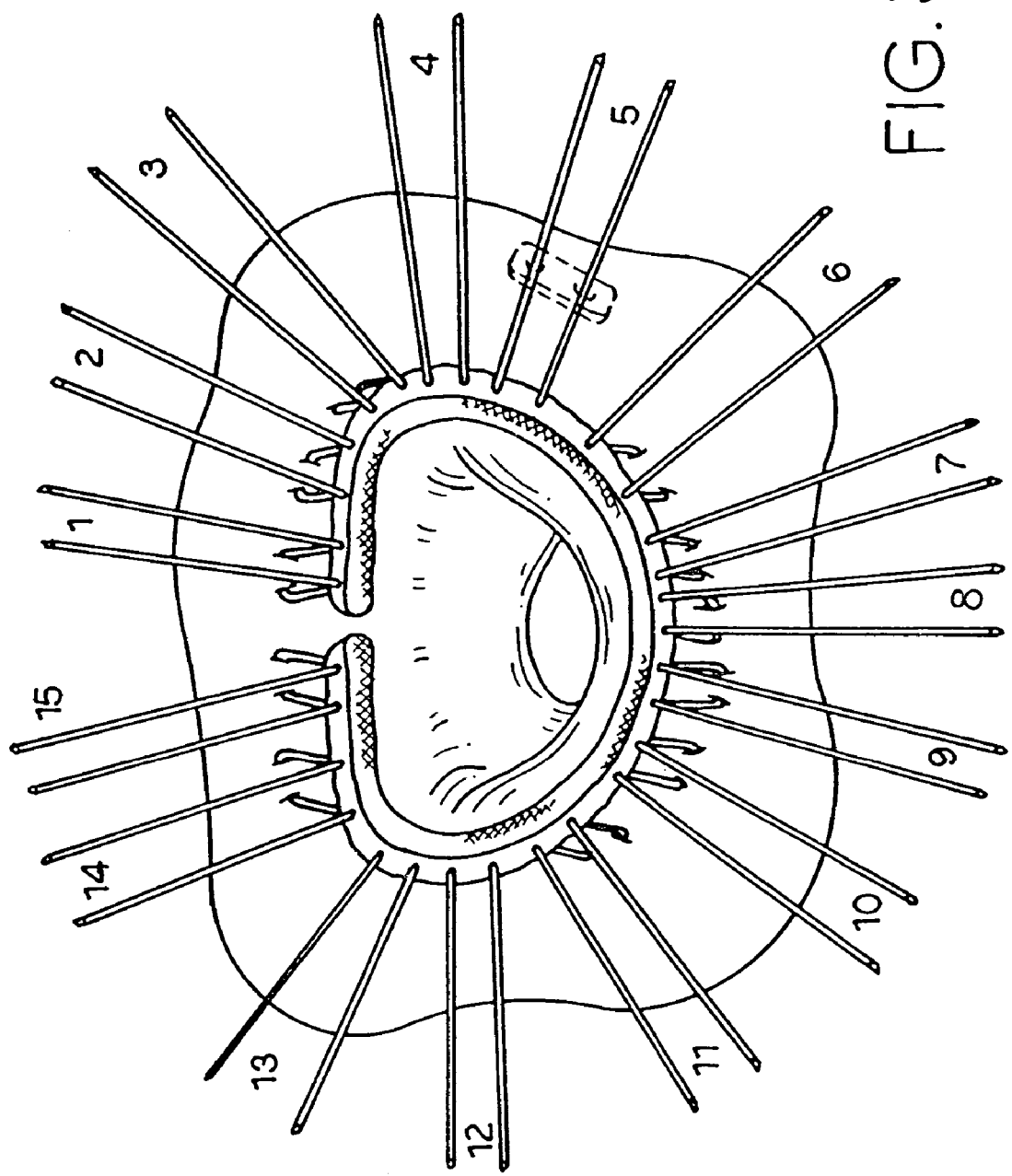

FIG. 35 shows a plurality of pairs of wire fasteners according to the present invention which have been placed into the mitral valve annulus and through a sewing edge of an anuloplasty ring.

Figure 36:
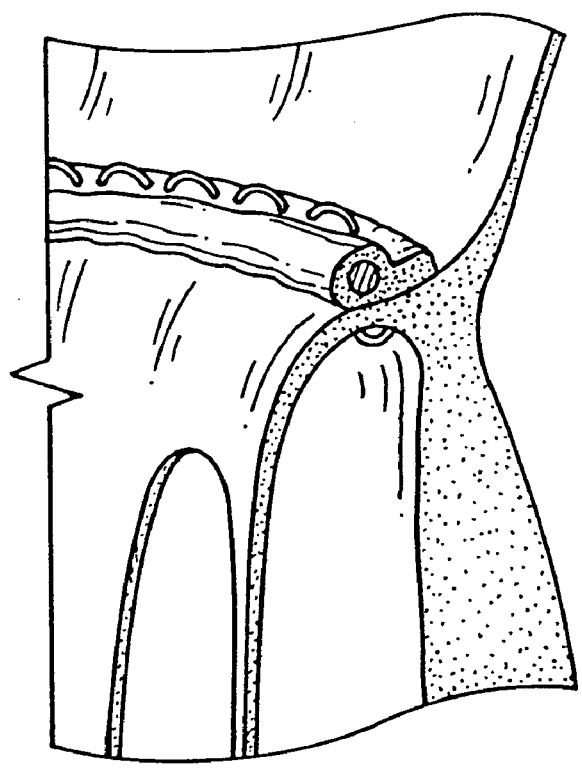

FIG. 36 shows wire fasteners of the present invention terminated into the sewing cuff anchoring a mitral valve in place according to the teaching of the present invention.

Figure 37:
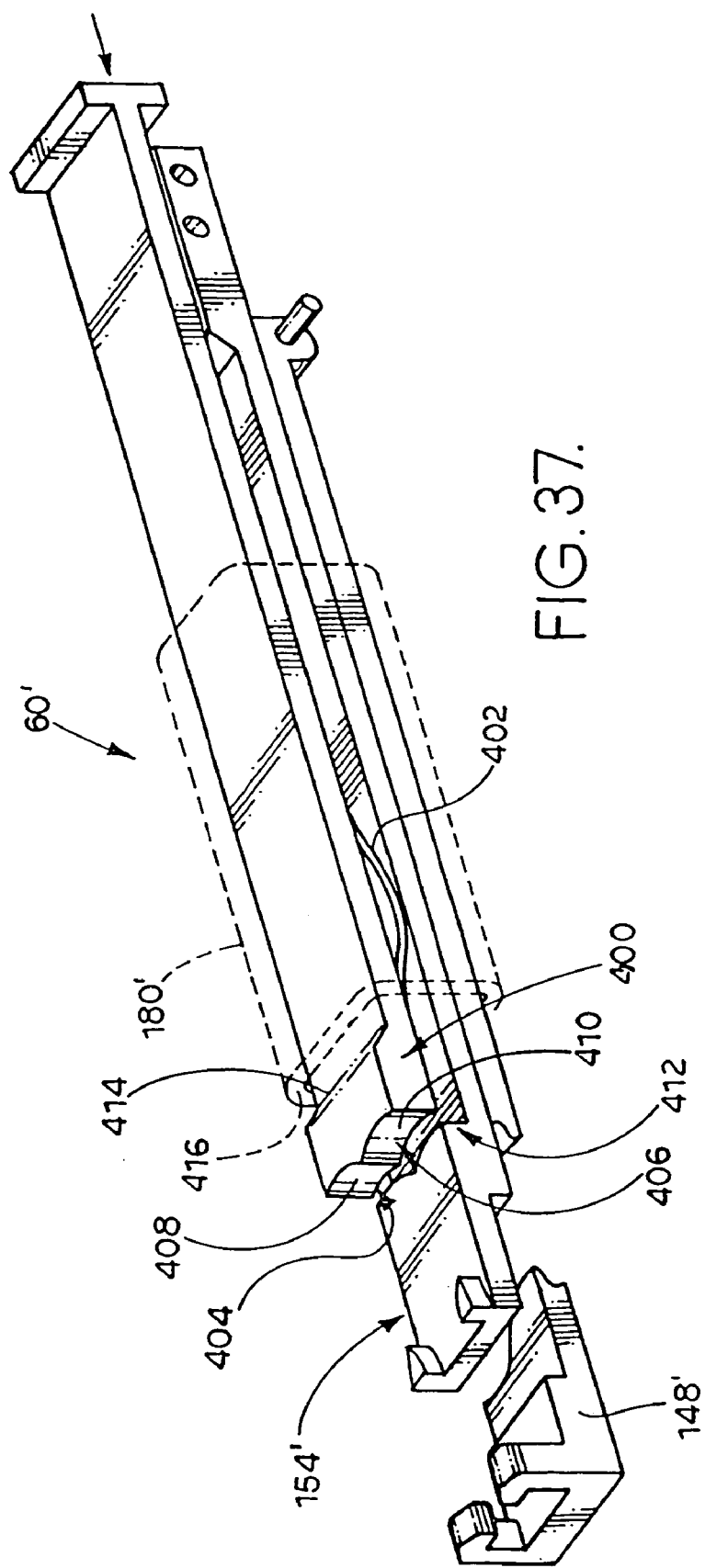

FIG. 37 shows an alternative form of the tool used to manipulate the fastener.

FIG. 38 is a cutaway side view of the alternative tool shown in FIG. 37 in a configuration immediately before the fastener legs are cut.

FIG. 39 is a view similar to that shown in FIG. 38 with the tool in a configuration immediately after the fastener legs are cut.

DETAILED DESCRIPTION OF THE PREFERRED EMBODIMENT OF THE INVENTION

Referring first to FIG. 1 for a broad overview of the means and method embodying the present invention, it is seen that a minimally invasive procedure is carried out by, after defining the necessary incisions, etc., placing the long leg wire fasteners of the present invention, then organizing the legs of those fasteners since the legs are long enough whereby some portion of the legs is located outside the patient. A sewing cuff of the prosthesis to be placed in the patient is placed on the fastener legs and guided down the legs into place. The prosthetic device, such as a heart valve in the best mode description here, is also placed on the legs of the fasteners and guided down the legs into place next to the sewing cuff. This is a relatively easy process since the fastener legs guide the items directly to the target area. A tensioning and forming tool is then guided down the legs of each individual fastener and operated. Operation of the tensioning and forming tool first immobilizes the legs adjacent to the prosthetic device, then cuts that portion of the legs that will not be needed to form the fastener into a staple-like anchor, then forms the remaining portion of each leg by bending it over into a staple-like configuration with the end of the leg abutting the device to press the device against the patient's tissue. The crown of the fastener, with a pledget if suitable, is located on the other side of the tissue. The forming tool terminates the stub, cutoff end to retain and anchor the prosthesis against the tissue. The fastener thus formed has no protruding elements that might create blood clots and is very stable. This immobilizing, tensioning, and forming process is repeated for each fastener. The long legs of the fasteners and the manipulation of the fasteners by immobilizing, tensioning and forming the fasteners by means of these long legs permits the fasteners to be placed and used as guides for the remaining portions of the procedure while forming the fasteners in a manner that is secure, efficient and safe for the patient.

Figure 1A:
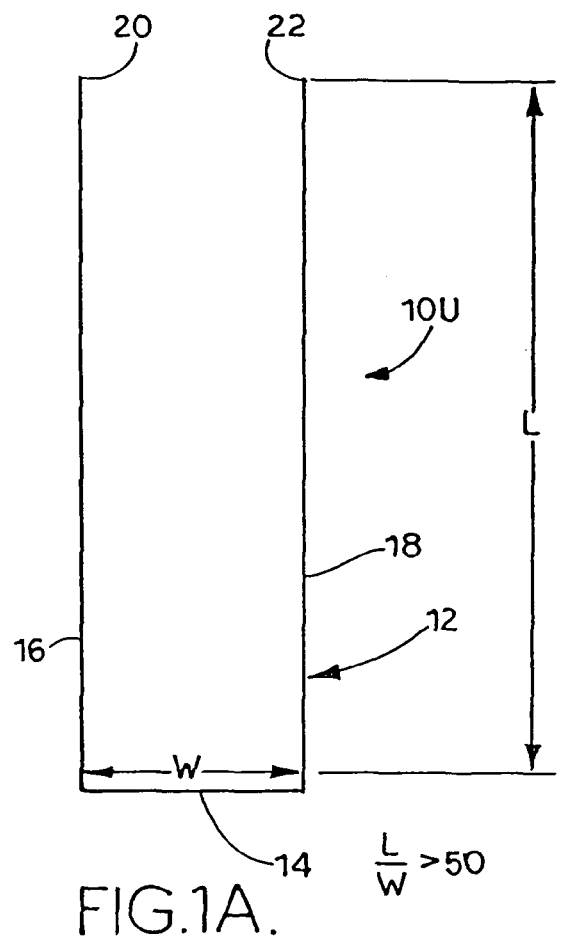
FIG. 1A shows a metal fastener embodying the present invention.
Figure 1C:
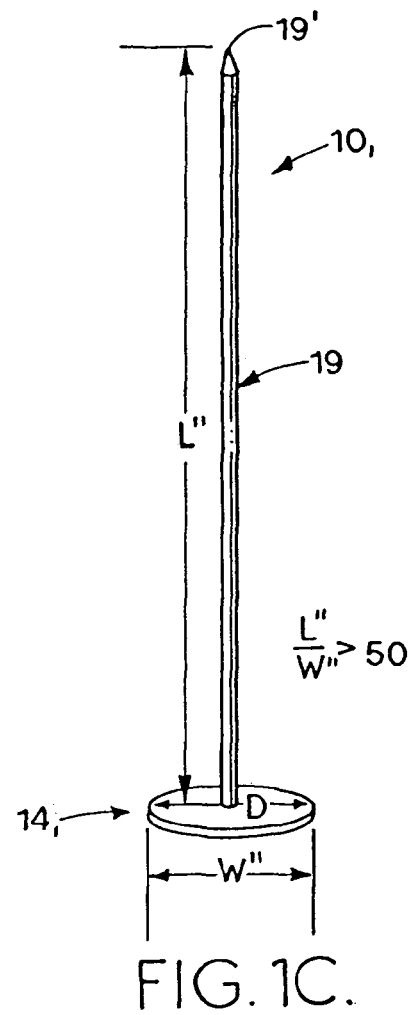
FIG. 1C shows a fastener having a single leg and an arcuate crown.
Figure 1B:
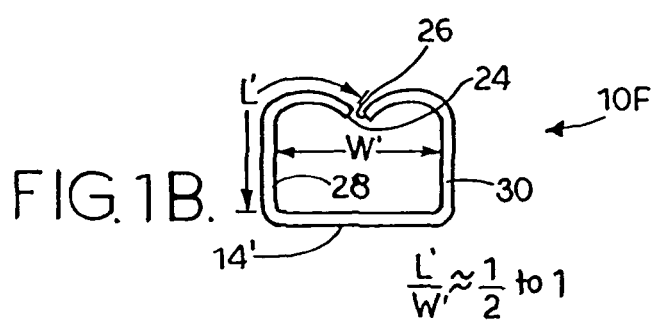
FIG. 1B shows the metal fastener of the present invention after that fastener has been cut and bent.
Figure 2:
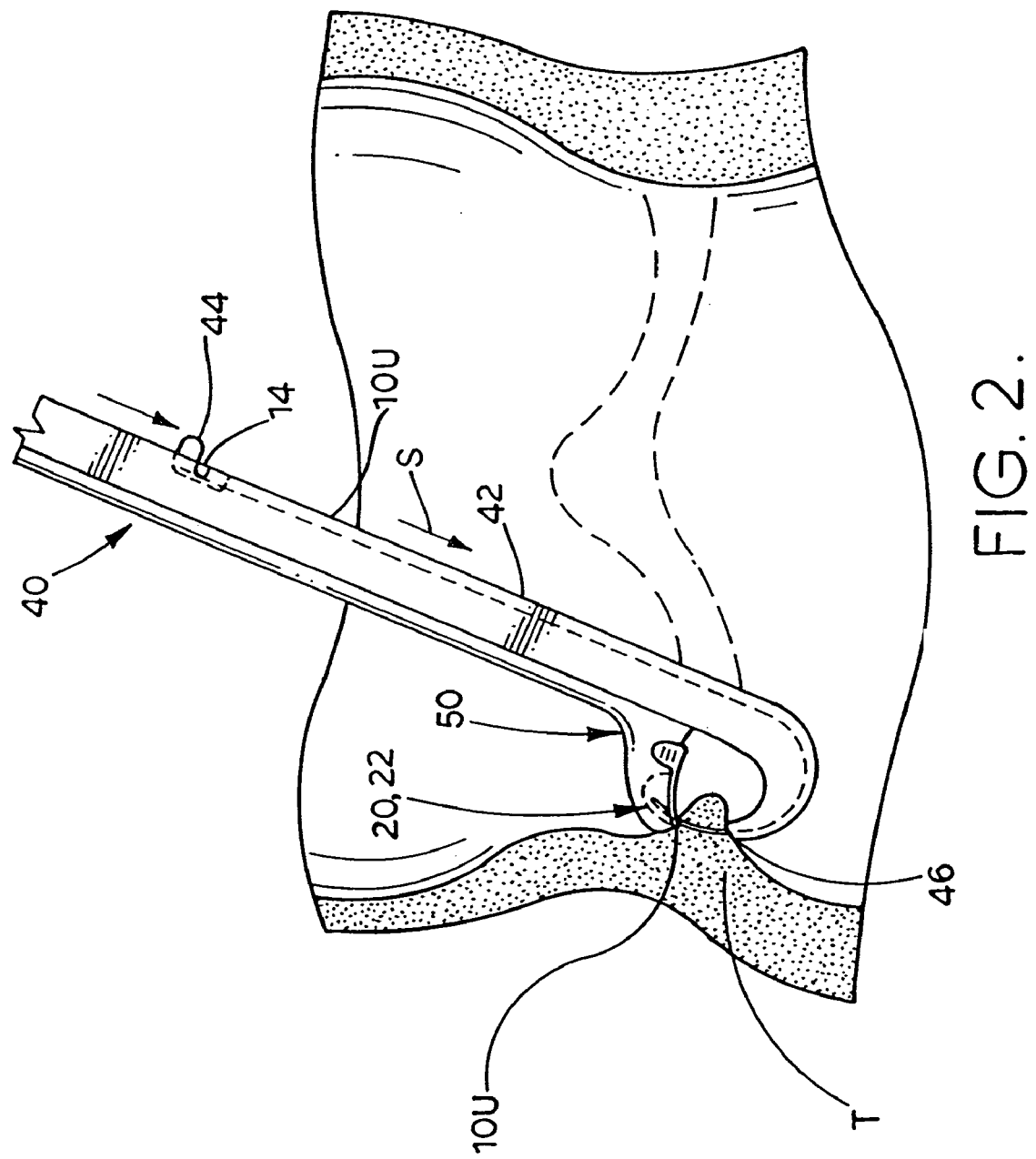
FIG. 2 shows a tool initially placing a fastener.

The fastener is specifically shown in FIGS. 1A, 1B and 1C, with FIG. 1A showing the unformed fastener 10U and FIG. 1B showing the formed fastener 10F. Unformed fastener 10U includes a U-shaped body 12 having a crown 14 and two long legs 16 and 18. Each leg extends from crown 14 to a pointed end 20 and 22. The fastener is one-piece metal and each pointed end is similar to the points on sutures that are pulled through tissue. Fastener 10U has a width dimension W measured between legs 16 and 18 adjacent to crown 14, and each leg has a length dimension L measured between the pointed end thereof and the beginning of the linear portion of the leg at the crown. As was discussed above, the legs are long enough so at least a portion thereof is located proximally to allow easy access to the legs when needed when the crown is seated against the patient's tissue to which a prosthesis will be anchored. Accordingly, length L can be as much as ten or twenty inches, while width W may be as small as 0.2 inches. Thus the ratio of length L to width W, L/W, can be as much as one hundred or more, and should be at least five so the legs will be long enough to extend out of the patient's body if needed. The lower L/W ratio will be used in situations where the fastener will be located close to the surface of the patient's body.

FIG. 1C shows a fastener $10_1$ with a single leg 19 and a load-spreading arcuate crown $14_1$ having a dimension D that can be either a diameter if the crown is circular or the major dimension of the crown is another shape, such as oval, or the like. Leg $14_1$ has a length L" measured from the crown to the leg tip 19'. The width W" of fastener $10_1$ is equal to dimension D. As indicated in FIG. 1C, L"/W" is greater than fifty, and can be more than one hundred if necessary.

As broadly mentioned above, the fastener is manipulated by immobilizing it from the legs, placing tension on it from the legs, cutting the legs and then bending the legs to form the formed fastener 10F shown in FIG. 1B. Once the fastener is cut, a large portion thereof is removed and new ends 24 and 26 are formed on cut legs 28 and 30 respectively. Fastener 10F has crown 14' which is similar to crown 14 and a width dimension W' which is very nearly equal to width W and is measured between legs 28 and 30 adjacent to crown 14'. Each cut leg has a length L' measured from adjacent to crown 14' to end of the leg, 24 or 26 along the long axis of the leg. As can be understood from FIGS. 1A and 1B, length L is considerably longer than length L', with length L' being similar to that of a staple and being in the neighborhood of ½ to 1 times the width dimension W' so the L/W ratio drops from one hundred or more for fastener 10U to ½ to 1 for fastener 10F.

Figure 3:
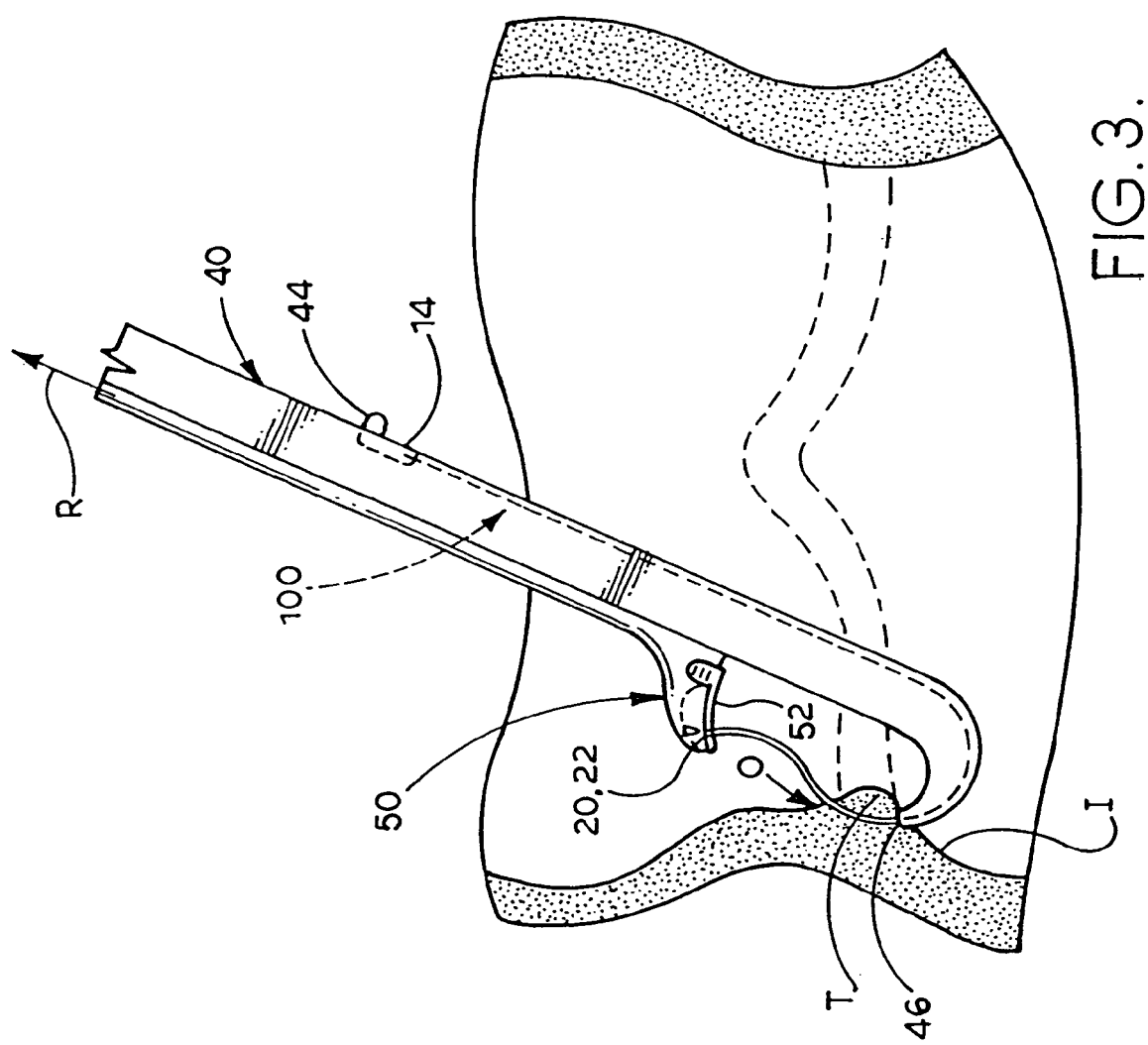
FIG. 3 shows a tool pulling a fastener through tissue during an intermediate step of the method of the present invention.
Figure 4:
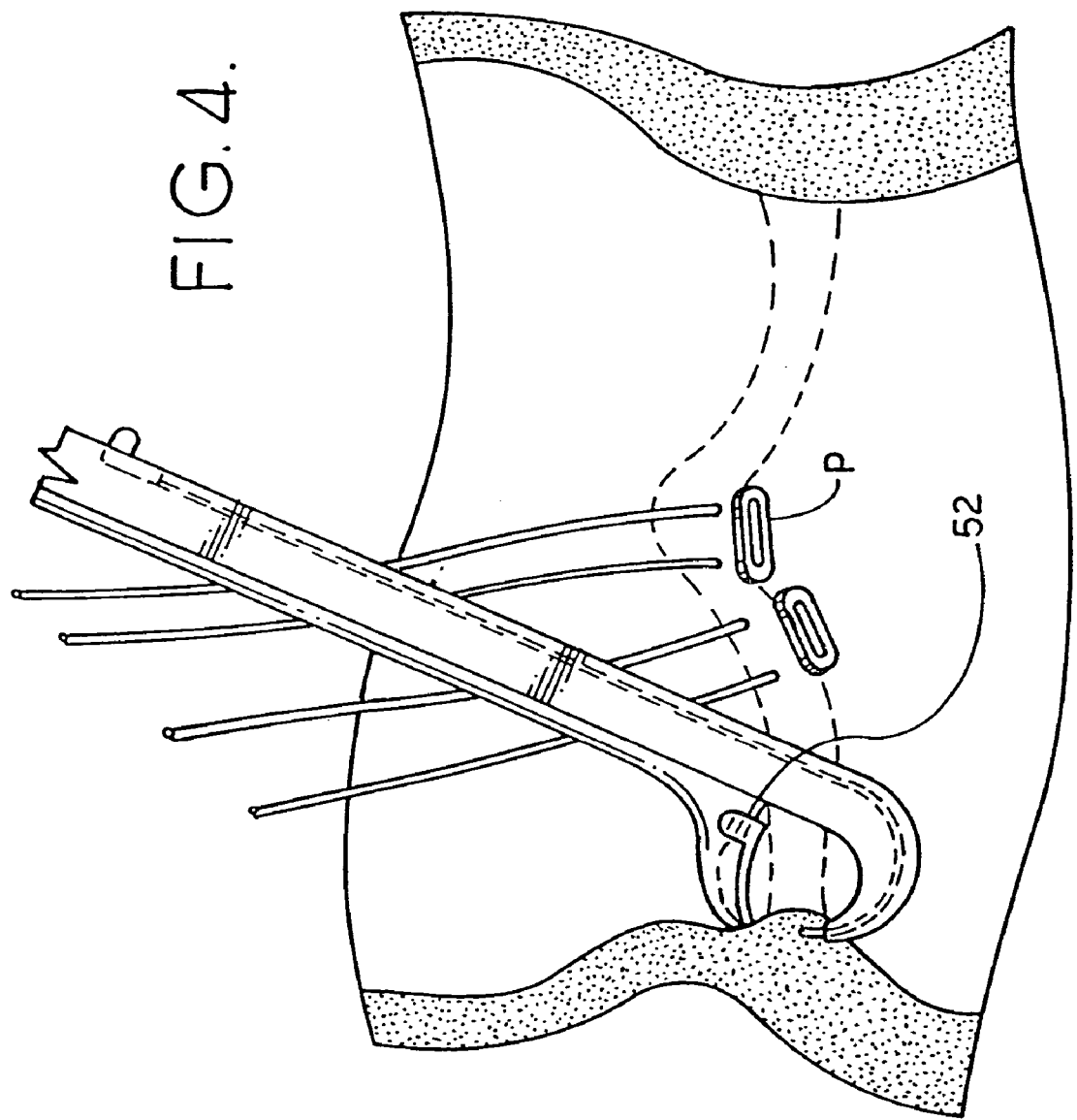
FIG. 4 shows a plurality of fasteners in place forming retaining features and a tool placing another fastener in a patient's tissue.
Figure 5:
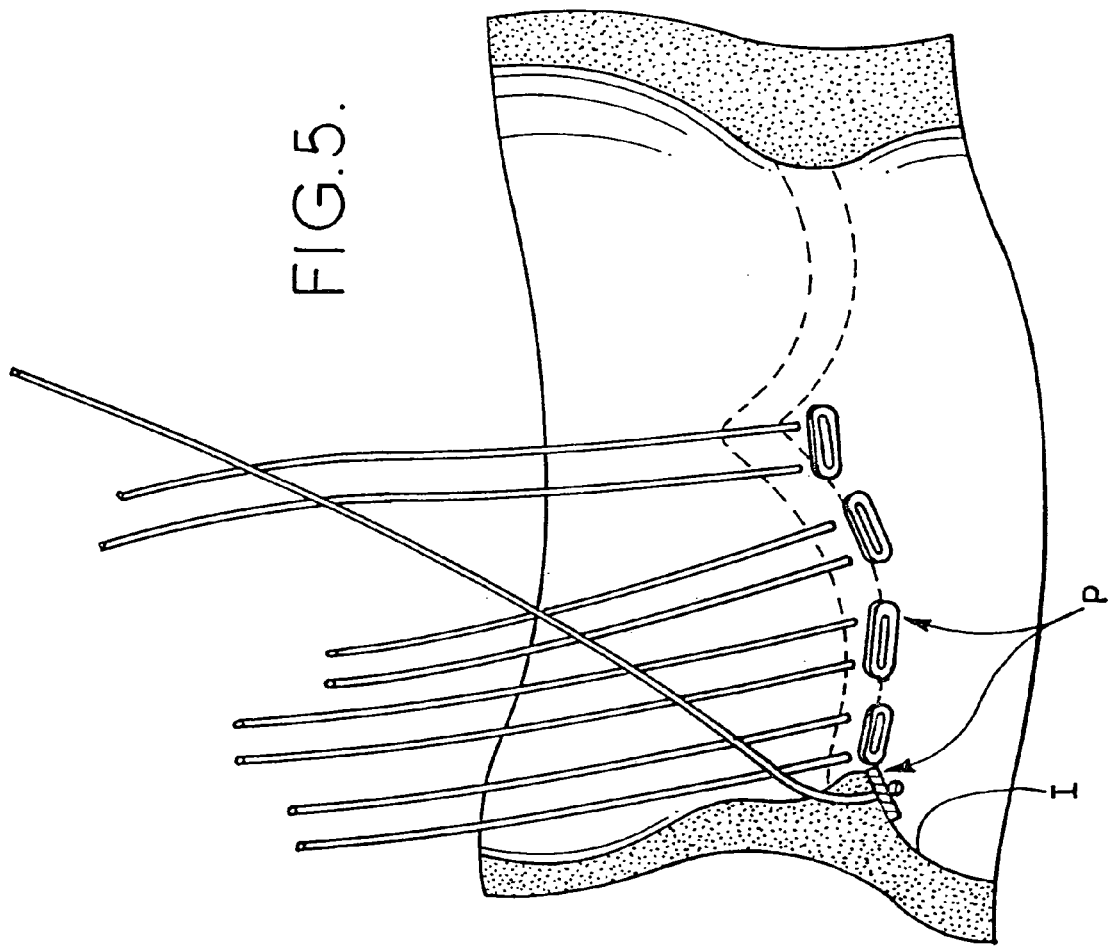
FIG. 5 shows a plurality of fasteners in place with the crowns on the inferior side of an aortic annulus.

Referring next to FIGS. 2-5, initial placement of fastener 10U will be discussed, along with a fastener placement tool 40. As shown, fastener 10U is movably stored on tool 40 with crown 14 proximally located with respect to the surgeon and pointed ends 20 and 22 located distally with respect to the surgeon. Tool 40 includes a body 42 on which fastener 10U is mounted to move toward the distal direction as indicated by arrow S in FIG. 2 under the influence of a crown follower 44 that is controlled by the surgeon from a handle of the tool located outside the patient's body. The surgeon manipulates tool 40 until a locating tip 46 is placed against the patient's tissue in the desired location. The surgeon then operates the handle of the tool to force crown follower 44 in the distal direction S and into contact with crown 14 to force the fastener in the distal direction S. Tips 20 and 22 penetrate tissue T at the desired location. Once the tips of the fastener have penetrated the tissue and emerges on the other side of the tissue, the surgeon operates another portion of the tool to move a fastener grabber 50 in the distal direction S. Grabber 50 has a portion 52 which will capture the legs of the fastener 10U once engaged with points 20 and/or 22. Protectors 52 can be formed of cork, urethane or other material that will securely hold the legs of the fastener once engaged by the points. As shown in FIG. 3, once the grabber is engaged with the pointed ends, the surgeon manipulates tool 40 to draw grabber 50, with the points 20 and 22 attached thereto, toward the proximal direction as indicated by arrow R in FIG. 4. Movement of grabber 50 in direction R draws fastener 10U through tissue T, and such movement is continued until crown 14 engages tissue T on side I thereof whereby crown 14 is in contact with side I and pointed ends 20, 22 are located on side O of tissue T so the tissue is interposed between crown 14 and pointed ends 20, 22. Legs 16 and 18 are long enough so when crown 14 is engaged against the tissue, at least some portion of the legs can be located outside the patient's body. Crown 14 will be pulled off tool 40 and the tool can be released from fastener 10U. This process is repeated for each fastener used in the process as indicated in FIG. 4 until all fasteners are set. As is also indicated in FIG. 4, a pledget P can be placed on each fastener so it is interposed between the crown of the fastener and the tissue. The pledget is placed on the fastener before the fastener is placed on tool 40. Pledgets and their functions and operations are well known to those skilled in the art and thus will not be discussed.

Figure 6:
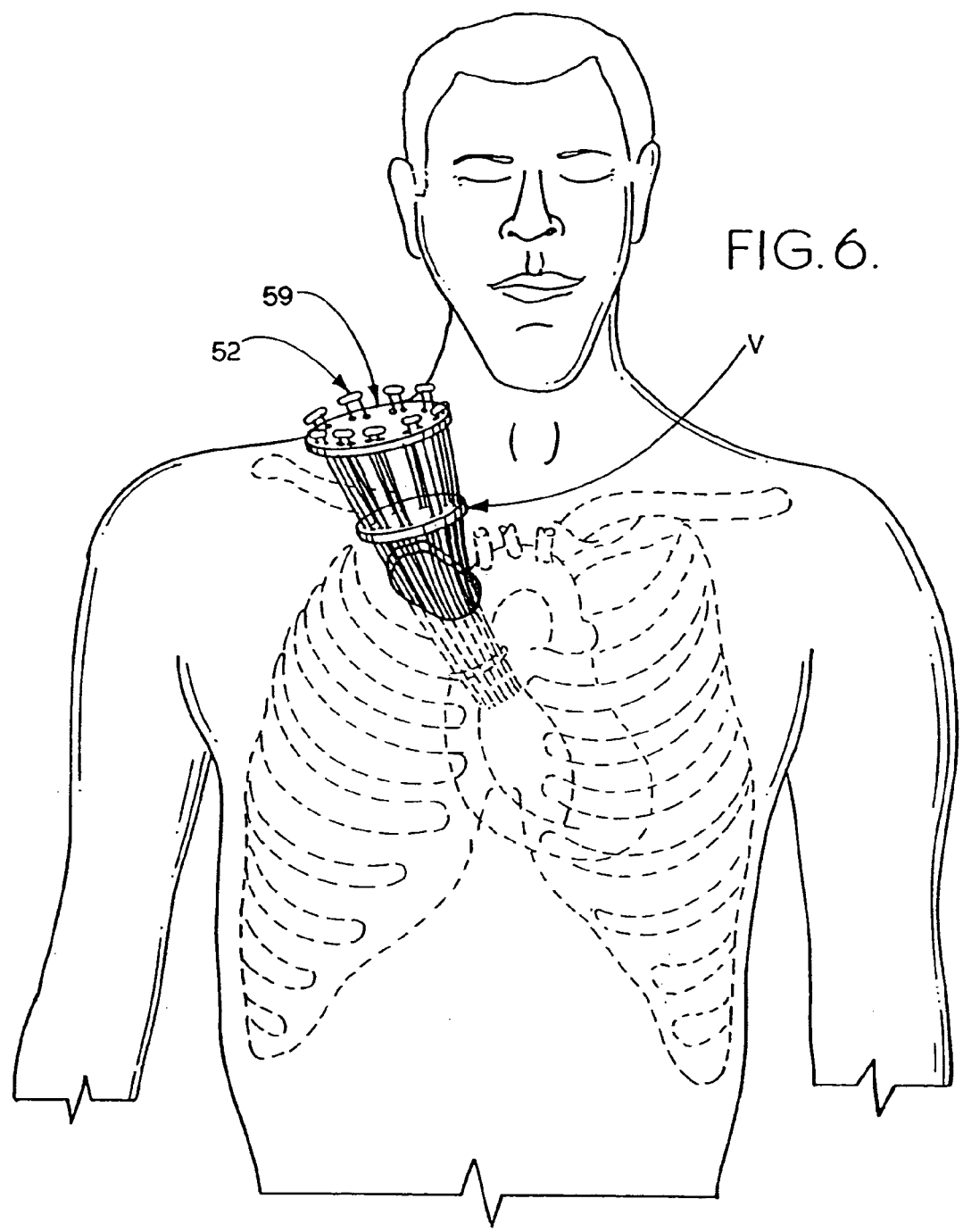
FIG. 6 shows a patient with a plurality of fasteners in an organizer.

As indicated in FIG. 6, the placed fasteners can be stored in an organizer 59 while the other fasteners are being placed. Protectors 52 can be placed on the fasteners to protect the surgeon against undue contact with the fastener pointed ends. A valve V is shown with wire legs engaged and the in the sewing cuff prior to being seated in the patient.

Figure 7:
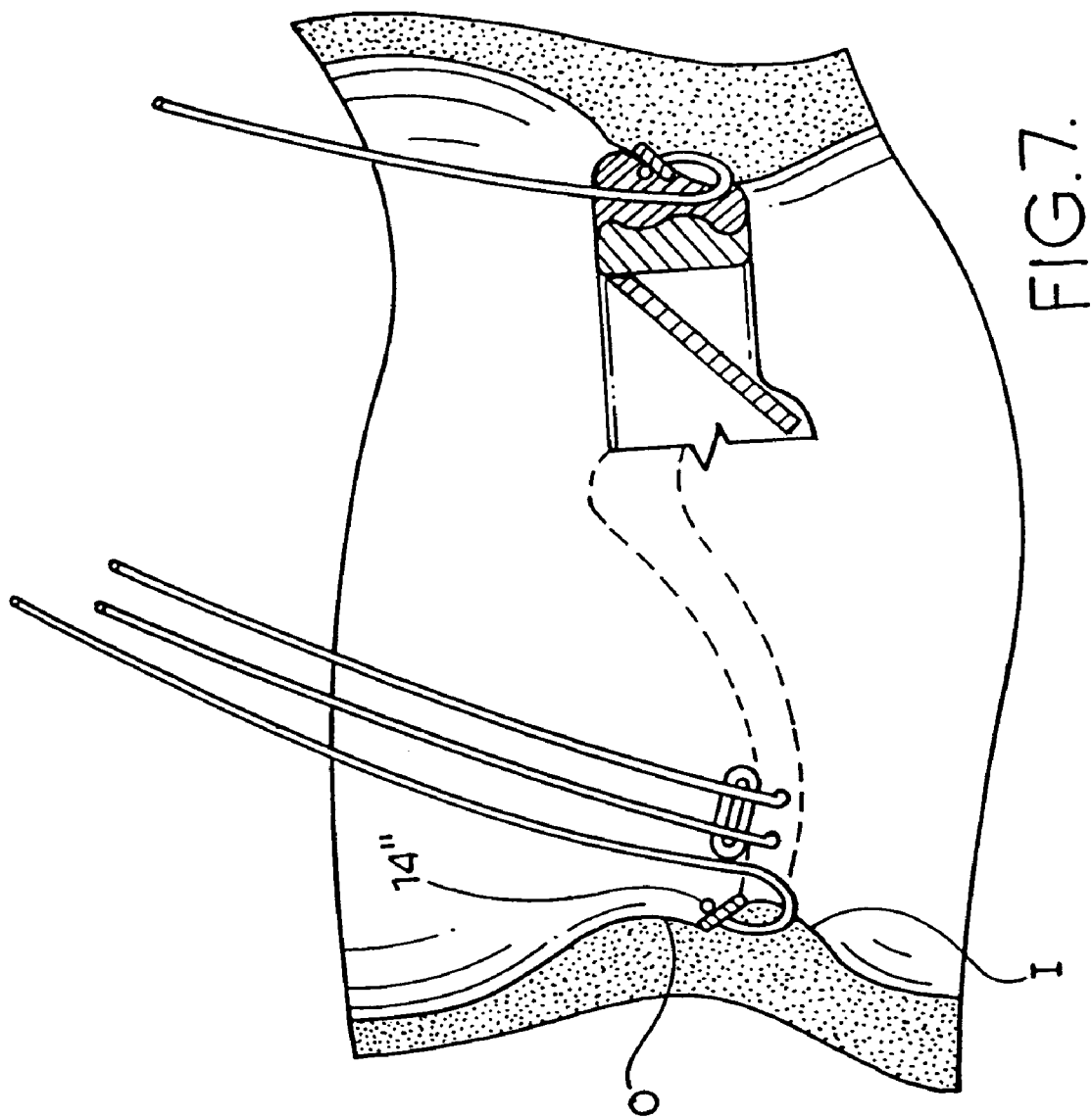
FIG. 7 shows a sectional view of a J-shaped fastener and a prosthetic valve anchored to the patient's tissue.

Alternative forms of the fasteners are shown in FIG. 7 in which the fasteners 10' are inserted through tissue T from side O toward side I whereby crown 14" is located on side O. Fastener 10' is J-shaped and is shown in FIG. 30B. Operation of tool 40 for fastener 10' is similar to that for fastener 10U just described, and thus will not be discussed. Fastener 10' has legs that extend out of the patient's body as just described for fastener 10U with pointed ends on the ends of these legs.

Figure 17:
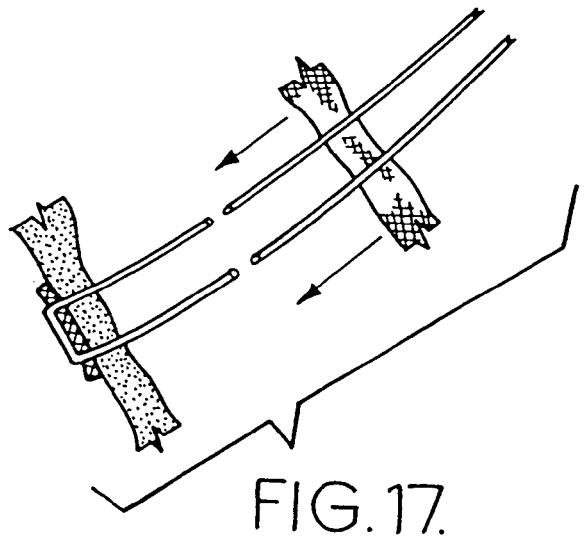
FIG. 17 shows a prosthesis being moved into position adjacent to the tissue on the legs of the fastener.
Figure 18:
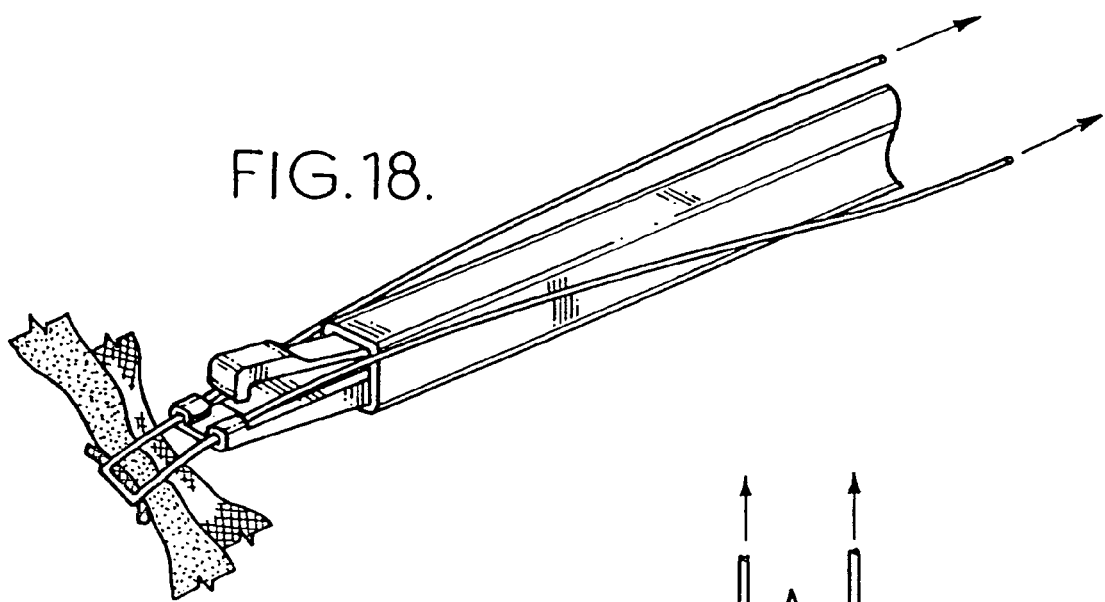
FIG. 18 shows the tensioning tool in position to cut the legs of a fastener to define the ends of the legs.
Figure 19:
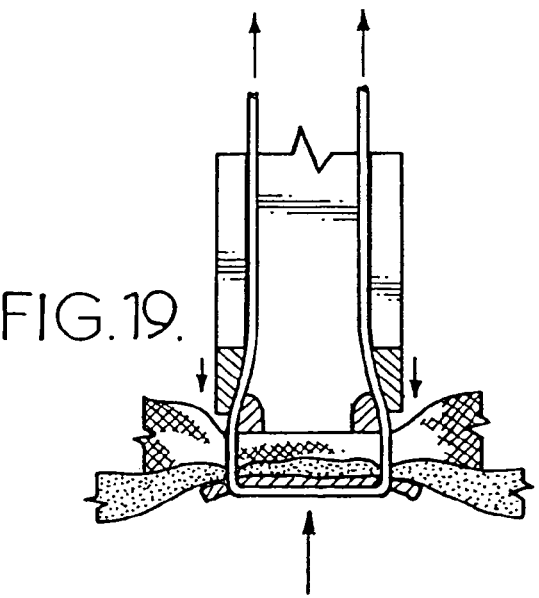
FIG. 19 shows the tensioning tool in position adjacent to a cuff.
Figure 20:
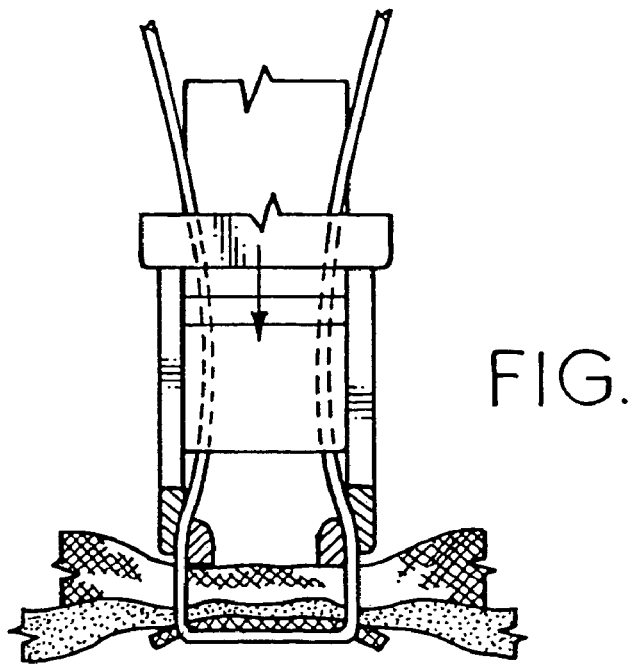
FIG. 20 shows the tensioning tool in position to cut the legs of the fastener.
Figure 21:
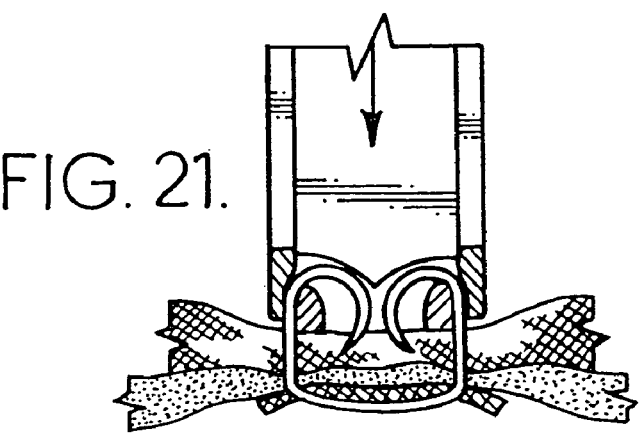
FIG. 21 shows the tensioning tool forming the fastener by bending over the cut legs into position against the tissue in the manner of a staple.

Once all of the fasteners are set, the sewing cuff of the prosthetic device is placed on the fastener legs outside the patient's body and slid down the legs until the device is in place. This step is illustrated in FIG. 17. The legs act like guides to guide the device directly and accurately into the desired location on the patient. The prosthetic device is then placed on the legs and slid down those legs into the desired position and location on the patient. This is indicated in FIG. 8.

Figure 8:
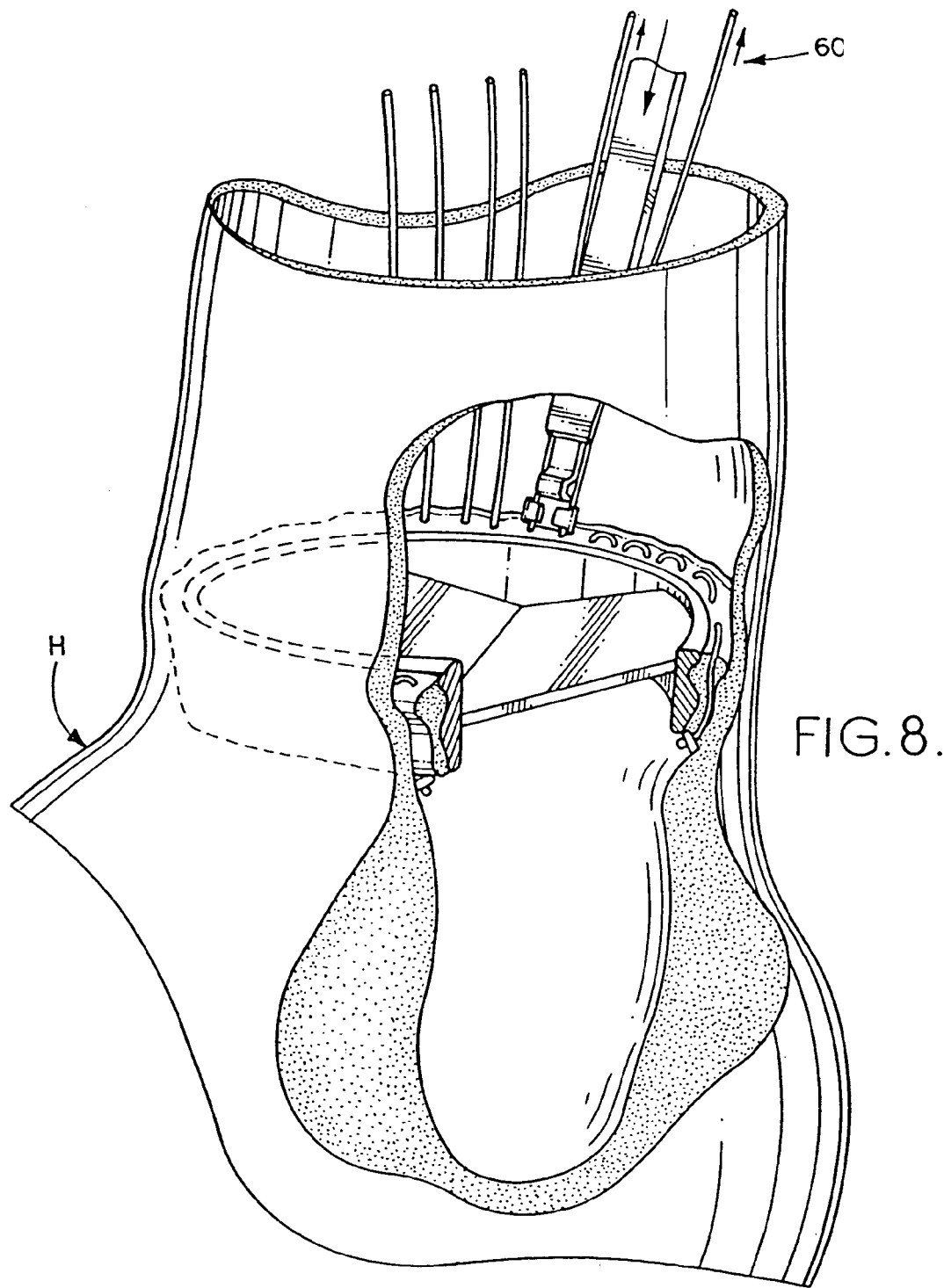
FIG. 8 shows a cutaway view of a prosthetic valve in place with a tensioning tool in place on one fastener.
Figure 9:
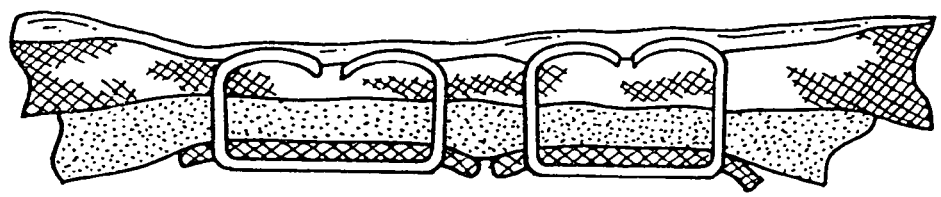
FIG. 9 shows a sectional view of a plurality of formed fasteners.
Figure 10:
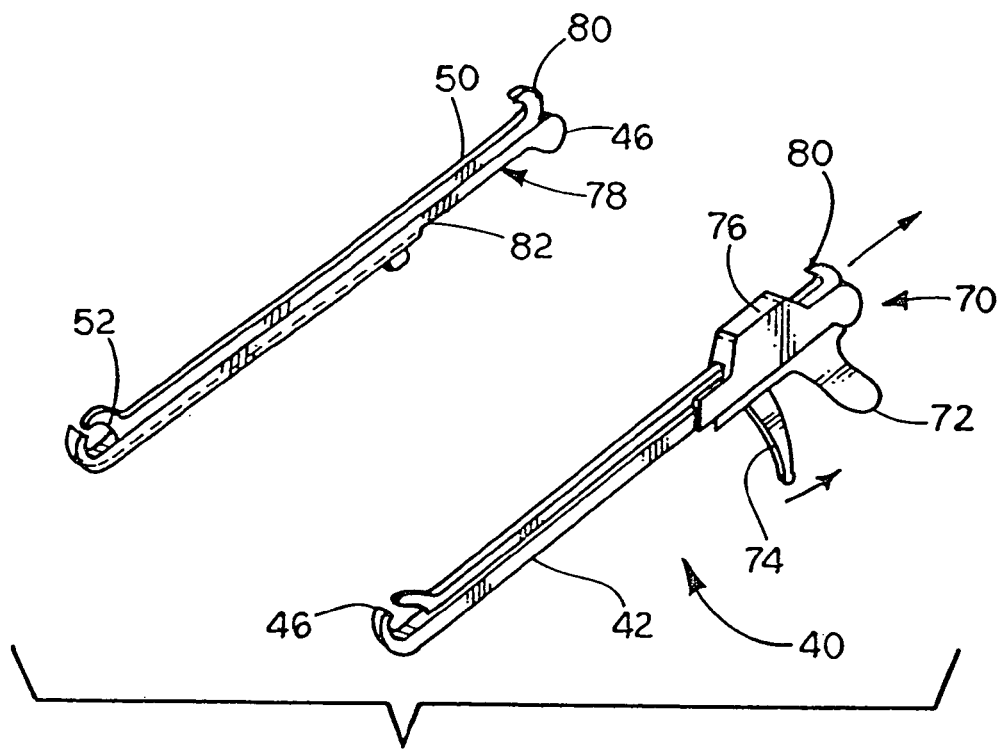
FIG. 10 shows the tool with a cassette containing a metal fastener removed from a handle of the tool.
Figure 11:
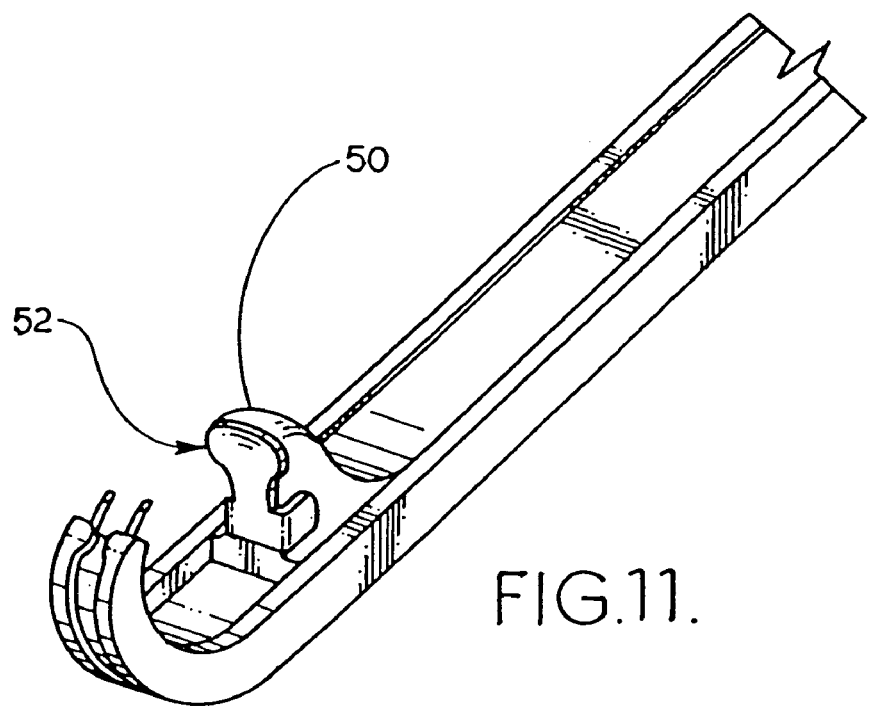
FIG. 11 shows the head of the tool with a fastener in place prior to the fastener being forced through tissue.

Once the prosthetic device is set, a manipulating tool 60 is placed on the fastener legs outside the patient's body and slid down the legs into the position shown in FIG. 8. A form of tool 60 will be discussed below, as will a form of tool 40 that is suitable for carrying out the method described herein on the fastener embodying the present invention. Tool 60 is operated by the surgeon from outside the patient's body, and operates on the fastener totally by means of the fastener legs. The fastener is immobilized via the legs, portions of the legs are cut off the immobilized fastener and the remaining legs are bent over from the leg side of the fastener into the formed configuration 10F shown in FIGS. 1B and 9. Tool 60 is then twisted until it is released from the formed fastener and then is withdrawn from the patient. This process is repeated for each fastener until all of the fasteners have been formed as shown in FIG. 9 to securely, accurately and precisely attach a prosthetic device to the patient. FIG. 8 shows a heart valve placed in an aorta associated with heart H; however, as discussed above, no limitation to heart valves is intended with this being intended as only an example of this invention.

Tool 40 is best shown in FIGS. 10-13. Tool 40 includes body 42 which extends from handle 70 to locating tip 46. Handle 70 includes a hand gripping portion 72 and a trigger 74 that is operated by squeezing in direction C shown in FIG. 10. A gear (not visible in FIG. 10) is rotated by the action of trigger 74. A sleeve 76 is located on top of the tool, and a cassette 78 is releasably mounted on the tool by the sleeve. Cassette 78 includes crown follower 46 on one end and tip locator 46 on the other end, with grabber 50 being slidably mounted on the cassette and having a manipulating handle 80 on one end thereof. Grabber 50 is slidably mounted on the body 78 so grabber can slide on the body 78 and these two elements can move with respect to each other. Body 78 includes a rack gear 82 that engages the gear operated by trigger 74 whereby operation of trigger 74 moves crown follower 46 in direction S. A fastener is placed in a track in body 78 to have the crown thereof engaged by follower 46. As will be understood, operating the trigger 74 moves the fastener 10U into position and forces pointed ends 20 and 22 through the tissue, then operation of handle 80 drives grabber into position to engage these pointed tips. Pulling handle 80 out of the patient in the proximal direction draws the fastener through the tissue and sets the crown against the tissue as discussed above. The fastener can be located in a disposable track located on body 42. Each time a fastener is set, a the track is removed, and a new track is placed on the body, with a new fastener on the new track. The tool is then ready for re-use to place the new fastener.

Figure 12:
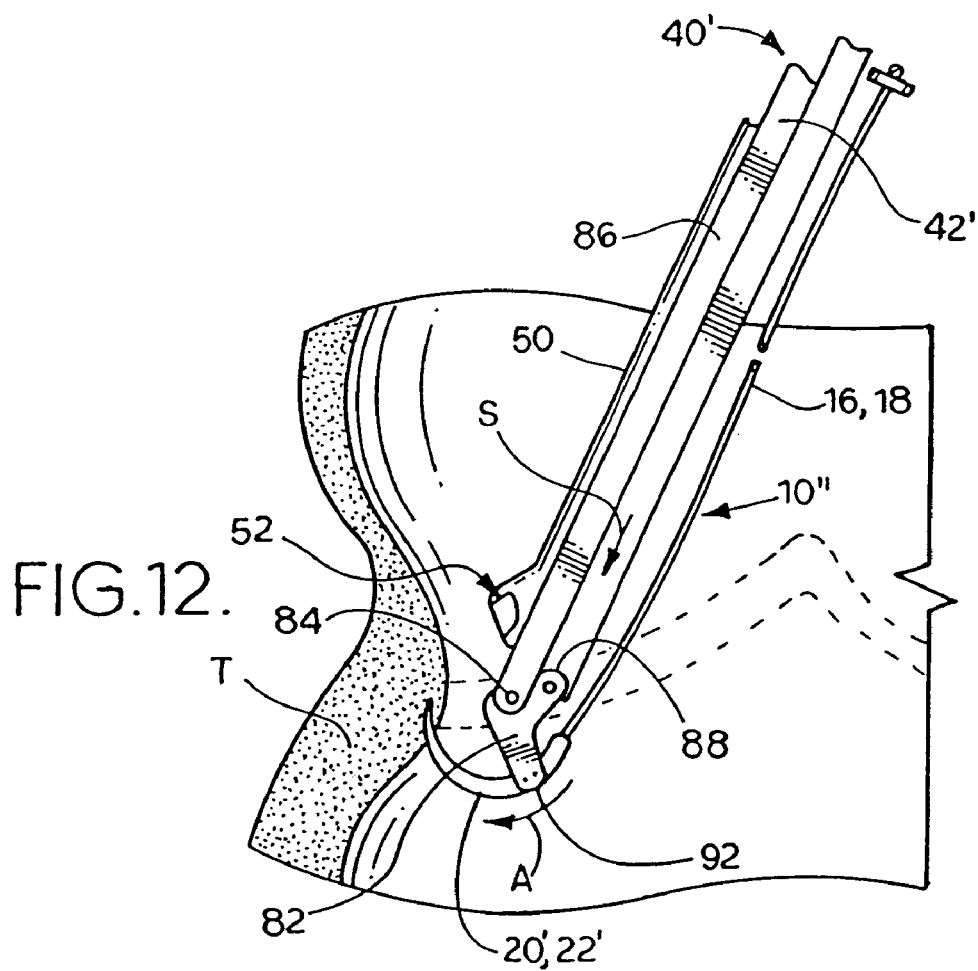
FIG. 12 shows an alternative form of fastener being positioned to be driven through the tissue by the tool.

An alternative fastener 10" is shown in FIGS. 30C and 30C1 and a tool 40' for placing fastener 10" is shown in FIG. 12. Tool 40' drives fastener 10" by grasping needle points 20' and 22' and driving them along an arc path A upwardly through tissue T. Fastener 10" includes legs 16' and 18' one end of which is connected to the crown and the other end of which has needle points 20' and 22' thereon. Points 20' and 22' are attached to the legs 16' and 18' by swaging or the like and can flex as necessary. Tool 40' has a body 42' attached to a handle at one end thereof, and having a pivot lever 82 on the other end thereof. Lever 82 includes a fulcrum 84 attached to a stationary member 86 of tool 40' and a first lever end 88 pivotally attached to an actuator rod 90 which is operated by the surgeon from outside the patient's body to move in direction S to set a fastener, and a second lever end 92 to which a fastener end 20' or 22' is releasably attached as by a sliding fit or the like. Tool 40' also includes a grabber 50 as described above.

To drive a pointed end 20' and 22' through tissue, the fastener is placed on the tool 40' with ends 20' and 22' engaged with lever end 92, and the tool is placed in the patient and manipulated until ends 20' and 22' are located in the desired spot on the patient. Then, actuator rod 90 is forced in direction S thereby rotating the pointed ends through arc A and through the tissue. The grabber 50 is then operated in the manner discussed above and the procedure is completed as discussed above.

Figure 13:
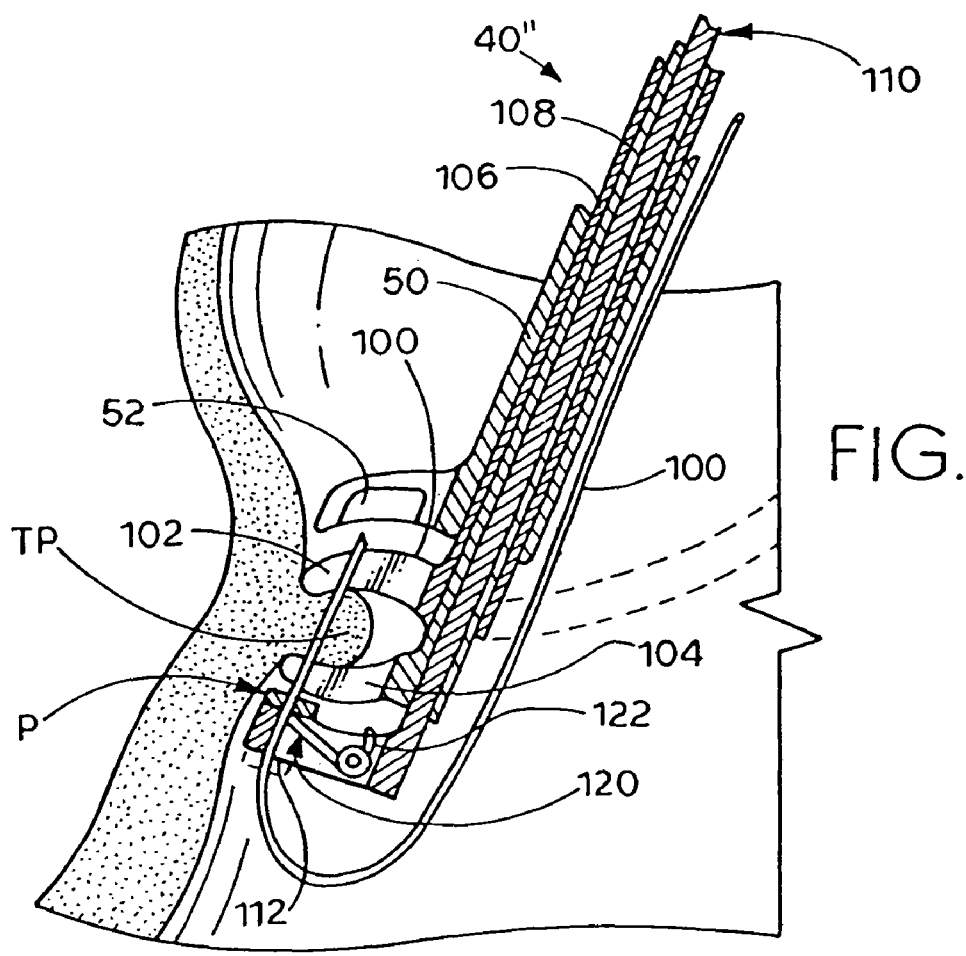
FIG. 13 shows a tool grasping tissue prior to driving a fastener through the grasped tissue.
Figure 14:
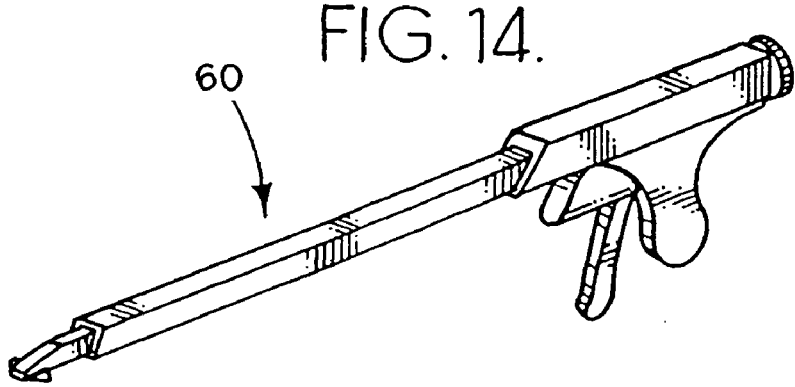
FIG. 14 shows a tool that can be used in the method of the present invention.
Figure 15:
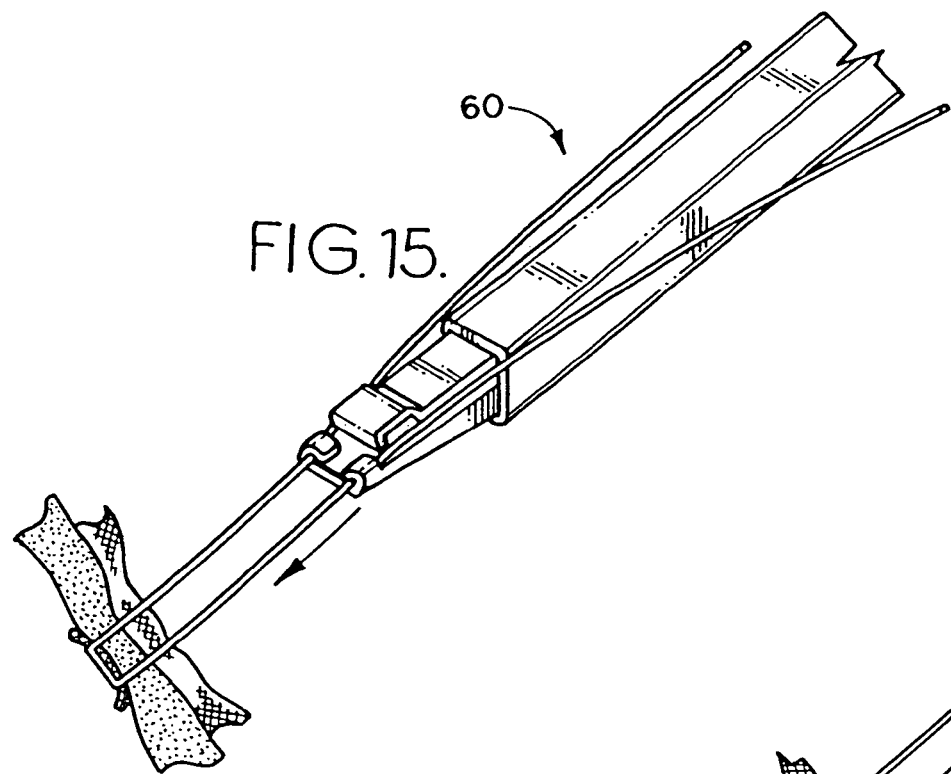
FIG. 15 shows a tool for tensioning, cutting and forming the fastener after the fastener has been driven through tissue by the tool and after the tool has been removed from the fastener and withdrawn from the patient.
Figure 16:
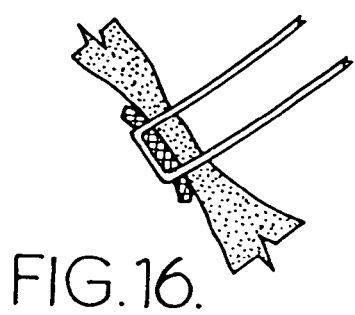
FIG. 16 is a view of the fastener in place on the tissue after the fastener has been driven through the tissue and before the tensioning tool has been placed on the fastener.

Yet another form of the tool is shown in FIG. 13 as tool 40". Tool 40" pinches the tissue prior to moving the fastener and thus includes a grasper mechanism 100. Mechanism 100 includes jaws 102 and 104, with jaw 102 being on driver 106 and jaw 104 being on driver 108 which are mounted on tool 40" to be movable with respect to each other. A fastener driver 110 is also mounted on tool 40" and has a driver element 112 pivotally mounted on one end thereof, with the other end being located in the handle of the tool outside the patient. Grasper mechanism 100 is operated by moving drivers 106 and 108 to draw the jaws 102 and 104 towards each other and together with tissue pinched therebetween.

Fastener driver 110 includes a one-way pawl 120 that operates a spring 122 to prevent rearward movement of the leg when driver 110 moves the leg 112 upward toward tissue TP which has been formed by the grasper mechanism. Element 112 is mounted on fastener driver 110. Graspers 102, 104 are proximally actuated to pinch the tissue targeted for fastener placement. Once the tissue TP is immobilized the tips 20, 22 of the fastener can be driven through the tissue toward the protector 52 into engagement with grabber 50. Grabber 50 is operated in the manner discussed above. As the tips of the fastener legs are drawn upward, the crown passes through pawl 120 releasing the fastener from the tool.

Figure 22:
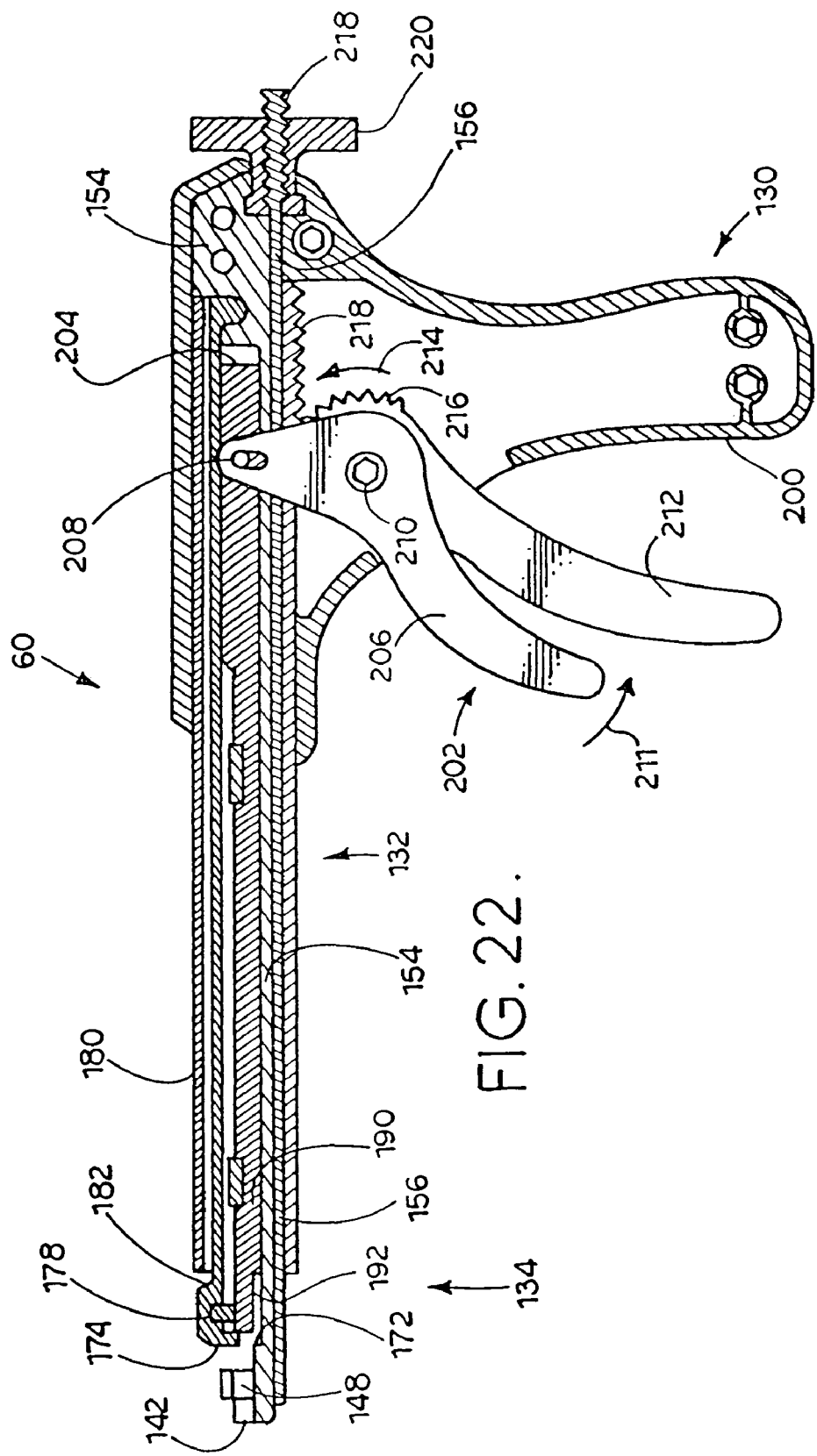
FIG. 22 shows a section of a tensioning, cutting and forming tool that can be used in the method of the present invention.
Figure 29:
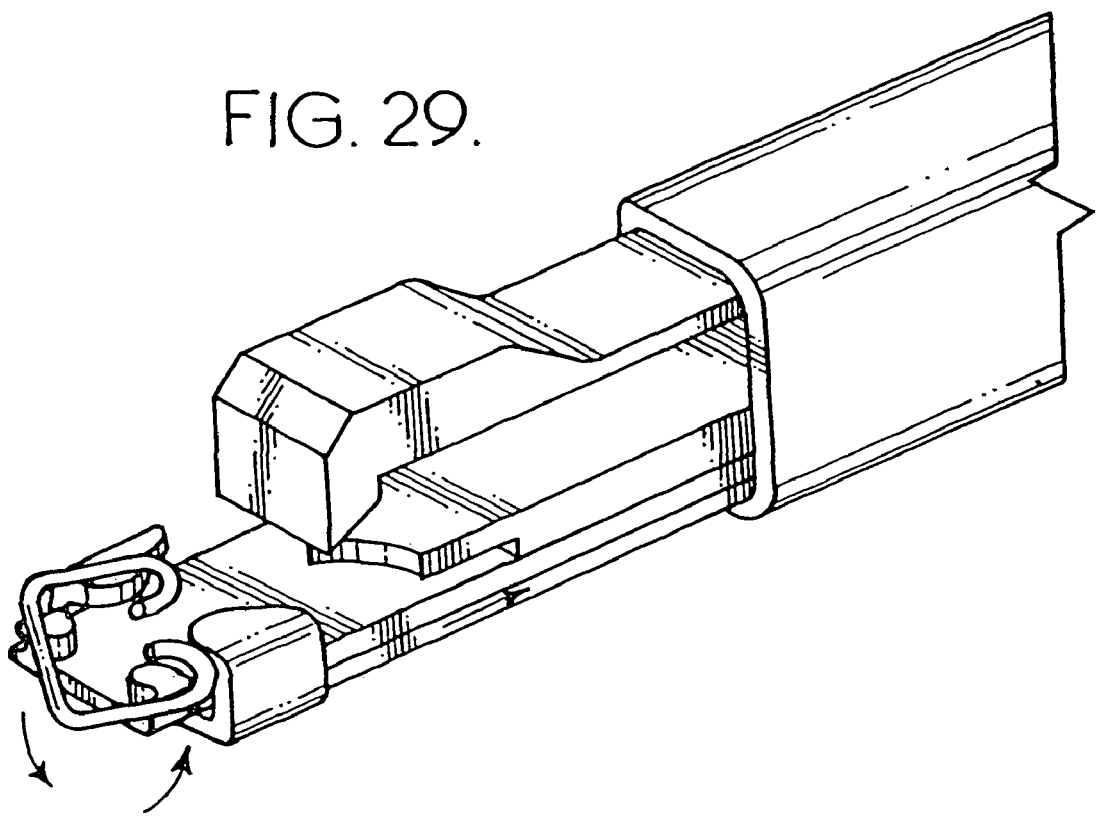
FIG. 29 shows the tensioning tool being removed from the formed fastener.

The tool 60 that immobilizes, manipulates, cuts and forms the fastener 10U into fastener 10F is shown in FIGS. 14, 15 and 18-29. As best shown in FIGS. 22-24, tool 60 includes a handle section 130 on one end of a body 132 which has a top section 134 on the end that is distal with respect to the surgeon. Handle portion 130 includes the elements required to operate the immobilizing, cutting and bending elements of tool 60 and tip portion 134 includes the elements required to carry out these functions on the fastener. For the sake of clarity of description, the tip portion will be discussed first so the operations of the tool can be used to explain the elements.

Referring to FIGS. 23-29, it is seen that the legs of the fastener are threaded through apertures defined between projections 140 and 142 on a stationary block element 144 and movable elements 146 and 148 respectively on a movable element 150. In the tool being described, elements 146 and 148 are movable relative to element 144. Therefore, for the sake of description, elements 146 and 148 will be referred to as being movable elements and element 144 will be referred to as a stationary element. However, no restriction is intended. Also, during the description, the stationary elements may also be referred to as a lock block to emphasize its function, and the movable elements may be referred to as pinch dogs to emphasize their function. As shown in FIG. 23, the stationary elements have apertures, such as aperture 152, defined therein, and the movable elements are positioned on the distal end of an element 154 which has a proximal end located in handle 130 which is anchored to the handle. The movable elements are mounted on the distal end of a movable driver rod 150 which has a proximal end in the handle 130 to be operated from that handle. The movable elements are moved relative to the stationary elements to close the movable elements around fastener legs that have been positioned in grooves 152 when tool 60 is placed on the fastener legs. The gaps defined between the movable elements and the lock blocks are maintained large enough to permit the tool to be slid down the legs of the fastener until the terminal end 160 thereof is located adjacent to the tissue. Once this occurs, the movable elements and the stationary elements are moved relative to each other to lock the fastener legs between the lock blocks and the pinch dogs as indicated in FIG. 24, with the relative movement of these elements being understood by comparing FIGS. 23 and 24. Once the legs are captured between the lock blocks and the pinch dogs, the fastener is immobilized. Other movable and stationary element employ arcuate angled surfaces which when engaged tend to wedge the wire legs tighter between each element for securely holding the legs.

The immobilized legs are then cut and bent into the FIG. 1B configuration by operating tool 60 using handle 130. As shown in FIGS. 25 and 26, tool 60 cuts the immobilized legs by means of a cutter mechanism 170 that includes a shearing edge 172 on stationary driver rod 154 and a cutting element 174 that has a cutting edge 176 on one end of a body 178 that extends in the proximal direction from tip 134. Shearing edge 172 is located with respect to the lock blocks 140 so that the distance between a crown located adjacent to the blocks 140 and the shearing edge is sufficient to form a cut leg having a length L when formed as shown in FIG. 1B. Cutter mechanism 170 further includes a sleeve 180 that is movably mounted on the tool to move in direction C shown in FIG. 25 when distally directed force is applied thereto from the handle end by the surgeon. As can be seen in FIG. 25, body 178 has a sloped shoulder 182 located to be slidably engaged by sleeve 180 when that sleeve is moved in direction C.

When sleeve 180 engages shoulder 182, it forces body 178 downwardly toward rod 154 in direction D shown in FIG. 25. Continued movement of sleeve 180 in direction C forces cutting edge 176 to cut legs 16 and 18 as shown in FIG. 26. The cut-off ends of the legs can be removed from the patient by the surgeon from the handle end of tool 60.

Referring next to FIGS. 27 and 28, it is seen how tool 60 is used to bend the cut legs into a staple shape. As shown, tool 60 includes an anvil mechanism 190 that includes a body 192 having one end thereof located outside the patient and having leg guiding surfaces 194 and 196 on the other end thereof. The surfaces 194 and 196 are shaped and positioned so that movement of the body 192 in direction F by pushing on the body from the handle end of the tool drives these surfaces against the immobilized and cut legs. Surfaces 194 and 196 are return surfaces and can be arcuate if suitable. The surfaces are shaped so that contact between the surfaces and the legs turns the legs inward as can be seen by comparing FIGS. 27 and 28. Once the legs have been turned, body 192 is retracted.

Once the legs have been formed and body 192 retracted, the fastener has been formed, and tool 60 can be removed. Removal is accomplished by releasing the legs from the pinch dogs and the lock blocks by moving the rods associated with those elements, and then simply twisting the tool to pull the lock blocks out of the formed fastener. The tissue and the sewing cuff as well as the other items captured by the fastener are soft enough to give when the tool is twisted so it can be removed from the fastener. This process is repeated on each fastener until all fasteners are formed into fasteners 10F. Once this is accomplished, the prosthetic device will have been anchored in place.

A preferred form of tool 60 is shown in detail in FIG. 22. The handle section of tool 60 includes a gripping handle portion 200 and a trigger portion 202. The anvil mechanism rod 192 has a proximal end 204 and is connected to a trigger element 206 by a pin 208. A pivot pin 210 is mounted on handle portion 200 and trigger element 206 pivots in direction 211 when operated. Moving the trigger element 206 in direction 210 moves the anvil body 190 in direction F shown in FIG. 28 to form the fastener. The handle section also includes a cutter handle 212 that is also pivotally mounted on the handle 200 to be moved in direction 214 by the surgeon. A gear 216 on handle 212 engages a rack 218 on cutter sleeve 180 to move that sleeve in direction C shown in FIGS. 25 and 26 to operate the cutter element as above discussed. The lock blocks 140 and 142 are on rod 154 which is held stationary with respect to handle 200 while the pinch dogs 146 and 148 are mounted on rod 156 that has a threaded element 218 on the end thereof adjacent to handle 200. A knob 220 has an internally threaded bore that threadably engages element 218. When the surgeon rotates knob 220, rod 156 is moved relative to the handle and thus relative to the lock blocks to close the pinch dogs on the lock blocks and thus capture the fastener legs between the pinch dogs and the lock blocks to immobilize those legs.

Figure 30A:
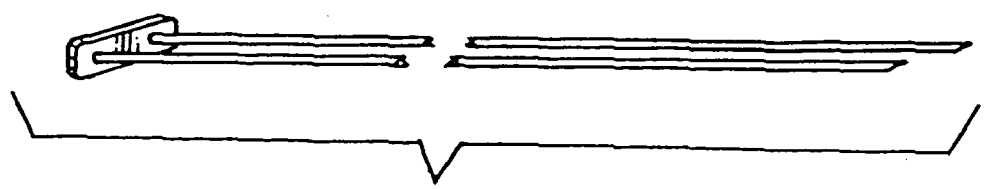
FIG. 30A is an alternative form of wire fastener with a linear crown instead of an arcuate crown as is in the preferred form of the fastener.

Other forms of the fastener can also be used, just so the fastener has legs that are very long with respect to the crown. Another form of fastener is shown in FIG. 30A as fastener 10''' and has a linear crown 14'''.

In some situations, the wire legs of the fastener may be cumbersome. In such situations, an alternative form of the fastener having thinner legs that might be more flexible can be used. Such an alternative fastener is shown in FIG. 30D as fastener 10T. Fastener 10T has legs 16T and 18T that are as much as seventy percent thinner than base 14T. The dimensions of the legs and the base being used to compare one to the other is the outer diameter of the legs and the outer diameter of the base.

However, as discussed above, even the thin legs of a fastener such as fastener 10T may not be desirable for a particular operation. Therefore, a fastener such as fastener 10S shown in FIGS. 30E, 30F and 30F1 could be used. Fastener 10S has a stiff base 14S and sutures 16S and 18S as the legs. The sutures 16S and 18S can be any suitable suture material. Base 14S can be metal if desired. Pointed ends 20S and 22S of fastener 10S are formed by needles or the like which are attached to the sutures as by swaging or the like. The suture can be attached to the base as shown in FIGS. 30F and 30F1 as by crimping or the like. Alternatively, the base can be hollow such as shown for fastener 10S' shown in FIGS. 30G and 30G1 and the suture legs 18S' and 20S' formed from a single one-piece suture 16S'/18S' that is attached to the base 14S' by crimping or the like. Suture 16S'/18S' can be any suitable suture material.

As was also discussed above, some situations require fastener legs that are longer than other situations. In the past, a surgeon would have to either predict the length of fastener required, or stop the surgical procedure to change fasteners to meet the requirements of a specific situation. However, as can be understood from the present disclosure, the fastener of the present invention being manipulable from entirely the legs thereof, can be cut as needed. That is, since the fastener is pulled into position using the legs thereof, and is then cut and bent as needed entirely from the leg side of the fastener, the surgeon can set individual fasteners and cut the legs as needed for each individual fastener. Thus, a fastener can have leg lengths that differ from the leg lengths of adjacent fasteners. The surgeon can determine the leg length needed for a particular situation after he sees the situation. In order to capture this feature of the fastener of the present invention that permits the fastener to be customized, the leg length will also be described as being indeterminate. The indeterminate length of the fastener permits the fastener to be customized as needed even in situ. As is also discussed above, even in the situation of the customized fastener, the leg length will be proper so that the formed fastener will not extend into the blood stream.

The means and method of the present invention have been disclosed above in relation to an aortic heart valve, but as mentioned previously, the means and method embodying the present invention can be applied to many different procedures. One example of these additional procedures is mitral valve replacement or repair. In the case of mitral valve insufficiency, a prosthetic anuloplasty ring can be attached to the outer periphery of the mitral valve annulus thus reshaping the mitral valve orifice to provide for better closure of the mitral valve leaflets.

FIG. 31 shows a top view of a mitral valve anuloplasty ring 300 with its "D" or elliptical shape. Section A-A shown in FIG. 32 shows a cross-section of the interior of the anuloplasty ring. The ring contains a semirigid core 302 which helps to maintain its shape so that the ring will reshape the annulus of the mitral valve into the normal elliptical configuration. The construction of the ring includes the core 302 wrapped in a sewing fabric 304 such as a dacron polyester. Some anuloplasty rings contain an elongated edge which is used for suturing the ring to the valve. An anuloplasty ring is used in cases where the mitral valve has become leaky due to a relaxation or severing of the chorda tendinea. Further descriptions of indication for use and surgical anatomy can be found in texts and articles such as *Illustrated Book of Cardiac Surgery* by Bradley Harlan, Albert Starr and Frederic Harwin.

FIG. 33 shows a cut-away view of a mitral valve. The valve leaflet configuration shown in FIG. 33 is much different than that of a tricuspid valve such as in the aorta. There is no defined annulus of the mitral valve. Since it is located in a lower pressure chamber, the tissues do not need to be as strong and therefore are not as well defined. Nonetheless, successful mitral valve surgeries where sutures are placed above the leaflets are successful in retaining the prosthesis in the mitral area. The wire fasteners around the annulus of the mitral valve have entrance points 306 and exit points 308.

FIG. 34 shows a wire fastener with the curved sharpened end penetrating the mitral valve annulus in an installation. One end of the wire fastener enters and exits the annulus of the valve and is pulled up outside the body thus placing the crown of the fastener within the annulus.

FIG. 35 shows fifteen pairs of wire fasteners of the present invention which have been placed into the mitral valve annulus and through the sewing edge of the anuloplasty ring. The anuloplasty ring will be slipped down the legs of the wire fasteners as described above and then seated in the annulus. The fasteners at the base of the anterior leaflet are placed so there is no gathering of this portion of the annulus. Fasteners at the commissures and along the posterior of the annulus are positioned closer together along the ring than they are on the annulus. The ring is then seated and the valve is tested by injecting saline into the ventricular cavity with a bulb syringe. The wire fasteners are terminated as discussed above with a wire termination tool as discussed above for the aortic valve.

FIG. 36 shows a cutaway of the mitral valve anuloplasty ring with terminated wire fasteners in the sewing edge on the outside of the anuloplasty ring.

A tool 60' is shown in FIGS. 37-39 and is an alternative form of tool 60. Tool 60' includes a sleeve 180' in which stationary element 148', movable element 154', anvil/cutter 400 and leaf spring 402 are located. Elements 148' and 154' operate in a manner similar to the corresponding elements discussed above. Tool 60' differs from tool 60 in that anvil/cutter 400 is a one piece element that replaces the anvil and the cutter elements in tool 60. Thus, anvil/cutter 400 includes a shearing edge 404 on one edge of a shaping end 406. End 406 includes two arcuate sections 408 and 410 that correspond to the arcuate portions on the end of the anvil in tool 60. A shearing shoulder 412 is defined on element 154' to cooperate with the shearing edge and the shaped end to cut and bend the fastener legs as shown in FIGS. 38 and 39. The leaf spring 402 biases the cutter/anvil 400 upward away from cutting position relative to the shearing shoulder 412. Anvil/cutter 400 also has a ramp 414 thereon in position to be slidably engaged by end 416 of sleeve 180' when that sleeve is moved toward the distal end of the tool. As discussed above, such engagement forces the shearing edge of the anvil/cutter downward so it cuts the legs as above described with regard to tool 60. The sleeve will overcome the bias of the leaf spring during the cutting and forming movements, but the spring moves the cutter away from the shearing shoulder when the sleeve is moved toward the proximal end of the tool. A detailed description of the operation will not be presented as one skilled in the art will understand this operation based on the teaching of this disclosure and the disclosure of FIGS. 37-39.

As can be understood from the foregoing disclosure, the length of the fastener legs of the fasteners and tools of the present invention can be adjusted as required for each particular application. The legs can be grasped at any location to be cut or simply bent as required. Thus, the fastener can be used in tissue that has varying thickness, or can be a "universal" fastener that can be used in nearly any application. The fastener can be customized for each particular application by simply adjusting the length of the leg using the forming tool described above and grasping the leg at the location on the leg desired to define the fastener needed for the particular application.

As discussed above, the means and method of the present invention is suitable for use in minimally invasive surgery. However, those skilled in the art can understand that the means and method of the present invention can be used in any surgical procedure, including open surgery. Accordingly, the present disclosure is intended to cover situations other than minimally invasive surgery.

In addition, the step of tensioning the suture legs prior to holding the legs stationary for cutting and forming could be tool assisted whereby the surgeon would only need one hand to complete this step thereby freeing his other hand. In order to make the tool easier to use and amendable to one-handed use, it would include an additional mechanism on the tensioning tool described above which applies the proper tension to each leg singly or together. Such a mechanism would include a longitudinal slide on each side of the tool body. A wire engagement head would be located on the slide track. This wire engagement head is connected to a constant force return spring. After pressing the wire legs through the leg immobilizing jaws at the distal end of the tool, each wire leg is installed in the tensioning head. A one-way pawl in the head grips the legs when the slide track is retracted thus properly tensioning the legs. These heads could also be attached to a constant force spring which would regulate the amount of tension applied regardless of where along the track the wire legs come up taut. In this way, the step of tensioning the legs would not require a second human hand once the legs were properly engaged in the instrument. Ratchets could also be employed to make the head retract with multiple strokes from an actuating trigger engaging the track.

It is understood that while certain forms of the present invention have been illustrated and described herein, it is not to be limited to the specific forms or arrangements of parts described and shown.

We claim:

1. A fastener apparatus for use in surgery comprising:
a body having a base and a leg extending from said base; said body having a width dimension; said leg having an initial pointed end, an unformed length dimension measured from said base to said initial pointed end that is long enough to extend out of a patient when the base is in anchoring position within the patient's body, the leg configured to be cut between the base and the initial pointed end to a formed length dimension measured between said base and a new end, with the new end located between the initial pointed end and said base such that the unformed length is greater than the formed length, the leg formed from material that is deformed when the leg is bent to force the new end back towards the base to secure the fastener to tissue;
a pledget on the body adjacent the base; and
a tool configured for holding and cutting the leg and for bending the new end after the leg is cut to force the new end back towards the base to secure the fastener to tissue.

2. The fastener apparatus defined in claim 1, wherein the unformed length dimension measured from said base to said initial pointed end is between ten and twenty inches.

3. A fastener apparatus for use in minimally invasive surgery comprising:
a U-shaped body having a base and two legs extending from said base; said body having a width dimension measured from one leg to the other; each leg having a pointed end and a length dimension measured from said base to the pointed end thereof that is long enough to extend out of a patient when the base is in anchoring position within the patient's body; the length dimension of each leg being greater than said width dimension by a factor of five or more, the body formed from material that is deformed when the leg is bent to force cut ends of the legs back towards the base to secure the fastener to tissue;
a pledget on the body adjacent the base; and
a tool configured for holding and cutting the leg and for bending the new end after the leg is cut to force the new end back towards the base to secure the fastener to tissue.

4. The fastener apparatus defined in claim 3, wherein the length dimension of said leg is greater than said width dimension by a factor of ten or more.

5. The fastener apparatus defined in claim 3, wherein the length dimension of said leg is greater than said width dimension by a factor of one hundred or more.

6. The fastener apparatus defined in claim 3, wherein the length dimension measured from said base to the pointed end is between ten and twenty inches.

7. The fastener apparatus defined in claim 3, wherein the U-shaped body includes an abrupt bend between the base and each leg.

8. The fastener apparatus defined in claim 3, wherein the tool comprises a cutter mechanism that is movable along the tool to cut the legs of the fastener held by the tool.

9. The fastener apparatus defined in claim 3, wherein the tool comprises an anvil mechanism movable along the tool for bending the new end after the leg is cut to force the new end back towards the base to secure the fastener to tissue.

10. A method of placing a fastener in a patient during surgery comprising:
providing a fastener for use in surgery having a body having a base and two legs extending from said base, each leg having a pointed end and a length measured from said base, said length being indeterminate;
locating the fastener inside a patient on one side of a tissue being operated on;
driving the pointed ends of the fastener through the tissue;
grasping the legs after the legs have penetrated the tissue;
tensioning the legs and moving the base of the fastener against the tissue;
immobilizing the legs on the other side of the tissue;
engaging the ends of the immobilized legs with a tool;
cutting the legs with the tool; and
bending each leg using the tool to deform the leg and force the end back towards the base of the fastener.

11. The method defined in claim 10 in which the step of immobilizing the legs is performed by grasping each leg on the side of the tissue opposite that of the base of the fastener whereby the tissue is located between the base of the fastener and any means used to immobilize each leg.

12. A method of placing a fastener in a patient during surgery comprising:
providing a fastener for use in surgery having a body having a base and two legs extending from said base, each leg having a point on one end thereof and a length measured from said base, said length being indeterminate;
locating the fastener inside a patient on one side of a tissue being operated on;
driving the pointed ends of the fastener through the tissue;
engaging the fastener only at the legs after the legs have penetrated the tissue;
tensioning the engaged legs and moving the fastener until the base of the fastener moves against the tissue;
engaging the ends of the immobilized legs with a tool;
cutting the legs with the tool; and
bending the legs using the tool to deform the leg and force the ends back towards the base of the fastener.

13. A method of placing a fastener in a patient during surgery comprising:
providing a fastener for use in surgery having a body having a base and a leg extending from said base, said leg having a point on one end thereof and a length measured from said base, said length being indeterminate;
locating the fastener inside a patient on one side of a tissue being operated on;
driving a pointed end of the fastener through the tissue;
using only the leg of the fastener, moving the fastener into position;
cutting the fastener with a tool between the base and the pointed end to form a new end on the leg; and
bending the new end using the tool to deform the leg and force the new end back towards the base of the fastener.

14. A method of placing a fastener in a patient during minimally invasive surgery comprising:
providing a fastener having a body with a formable portion and having a base and a leg extending from said base; said body having a width dimension; said leg having a pointed end;
locating the fastener inside a patient on one side of a tissue being operated on;
driving the pointed end through the tissue;
grasping the leg after the leg has penetrated the tissue;
tensioning the leg and moving the base of the fastener against the tissue;
immobilizing the leg on the other side of the tissue with a tool;
cutting the leg with a tool between the base and the pointed end to form a new end on the leg;
engaging the end of the immobilized leg; and bending the leg using the tool to deform the leg and force the end back towards the base of the fastener.

15. The method defined in claim 14 including placing a pledget on the fastener adjacent to the base.

16. The method defined in claim 14 including placing a prosthesis on the fastener from the pointed end and moving the prosthesis on the fastener leg into position adjacent the tissue.

17. The method defined in claim 14 including grasping the tissue prior to driving the pointed end through the tissue.

18. The method defined in claim 14 including placing a plurality of fasteners.

19. The method defined in claim 18 including a step of organizing the fasteners.

20. The method of claim 14, wherein the tool comprises a cutter mechanism and wherein cutting the leg comprises moving the cutter mechanism along the tool to shear the leg.

21. The method of claim 14, wherein the tool comprises an anvil mechanism, and wherein bending the leg comprises moving the anvil mechanism along the tool to deform the leg.

* * * * *